US007131966B1

(12) United States Patent
Tamari

(10) Patent No.: US 7,131,966 B1
(45) Date of Patent: *Nov. 7, 2006

(54) AUTOMATED MEANS TO REMOVE AIR FROM VENOUS BLOOD DURING CPB

(76) Inventor: Yehuda Tamari, 21 Singworth St., Oyster Bay, NY (US) 11771-3703

( * ) Notice: Subject to any disclaimer, the term of this patent is extended or adjusted under 35 U.S.C. 154(b) by 0 days.

This patent is subject to a terminal disclaimer.

(21) Appl. No.: 10/915,000

(22) Filed: Aug. 9, 2004

Related U.S. Application Data

(62) Division of application No. 09/795,782, filed on Feb. 28, 2001, now Pat. No. 6,773,426.

(51) Int. Cl.
  A61B 19/00 (2006.01)
  A61M 37/00 (2006.01)
  A61M 1/14 (2006.01)

(52) U.S. Cl. .................... 604/406; 604/6.15; 422/44; 128/DIG. 3

(58) Field of Classification Search ............ 422/44–48; 604/4.01, 5.01, 6.01, 6.1, 6.07, 7, 6.09, 6.11, 604/6.14–6.16, 403–411, 317, 327, 319–324, 604/132, 151, 153, 246, 249; 128/DIG. 3
See application file for complete search history.

(56) References Cited

U.S. PATENT DOCUMENTS

| 4,500,308 A | * | 2/1985 | Kurtz et al. ............... 604/6.15 |
| 4,643,713 A | * | 2/1987 | Viitala ....................... 604/6.15 |
| 5,318,511 A | | 6/1994 | Riquier |
| 5,382,227 A | | 1/1995 | Riquier |
| 5,876,611 A | | 3/1999 | Shettigar |
| 6,017,493 A | * | 1/2000 | Cambron et al. ............. 422/44 |
| 6,113,575 A | * | 9/2000 | Viitala et al. ............... 604/132 |
| 6,302,860 B1 | * | 10/2001 | Gremel et al. ............. 604/6.09 |
| 6,773,426 B1 | * | 8/2004 | Tamari ....................... 604/406 |
| 6,773,670 B1 | * | 8/2004 | Stringer et al. ............... 422/44 |

OTHER PUBLICATIONS

Sistino JJ, Michler RE, and Mongero, LB Laboratory evaluation of a low prime closed-circuit cardiopulmonary bypass system. J Extra Corpor Technol. 1993;24(4):116-9.

* cited by examiner

*Primary Examiner*—Patricia Bianco

(57) ABSTRACT

Venous reservoirs are interposed between the patient and the arterial pump and serve to remove air bubbles and provide compliance that accommodates variations in the volume of blood circulating in the extracorporeal circuit during cardiopulmonary bypass (CPB). The invention is a reservoir that incorporates automated means to remove air bubbles from the venous line prior to the blood entering the arterial blood pump. In another form, the reservoir includes means that handles foam prior to the blood entering the blood pump. In yet another form, the invention is means that improve air removal in a soft shell venous reservoir. These features are applicable to CPB circuits using gravity drainage or vacuum assisted venous drainage.

66 Claims, 13 Drawing Sheets

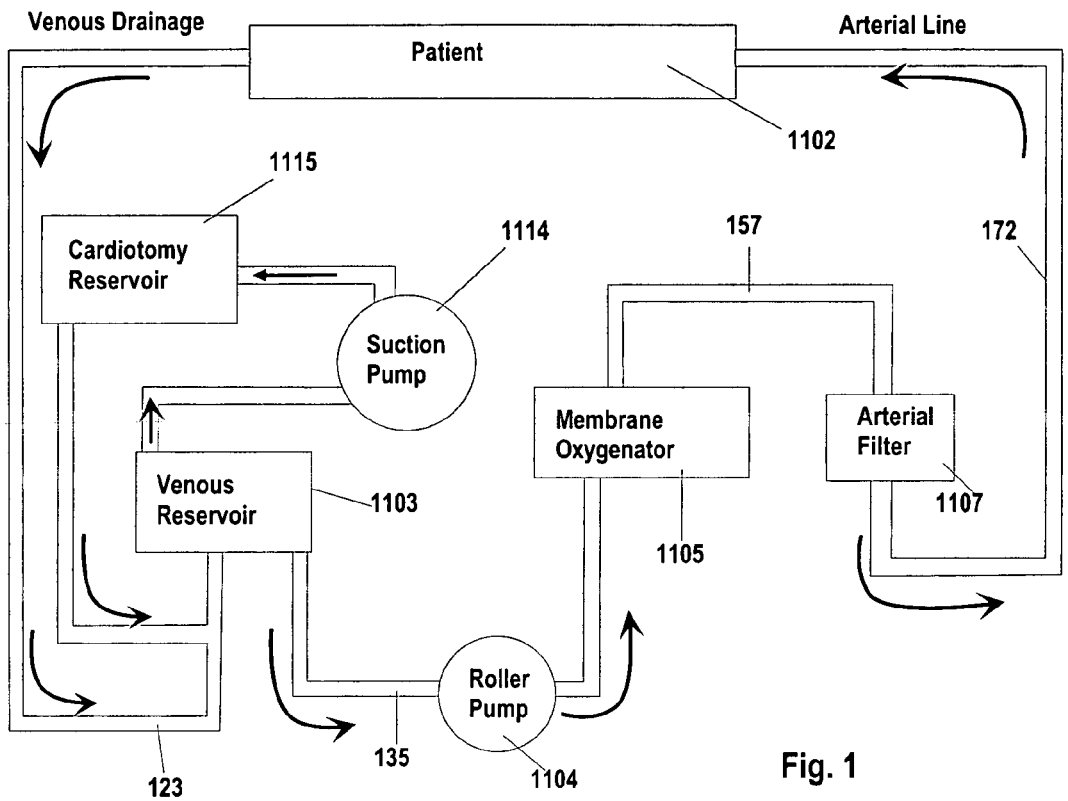
Fig. 1
PRIOR ART
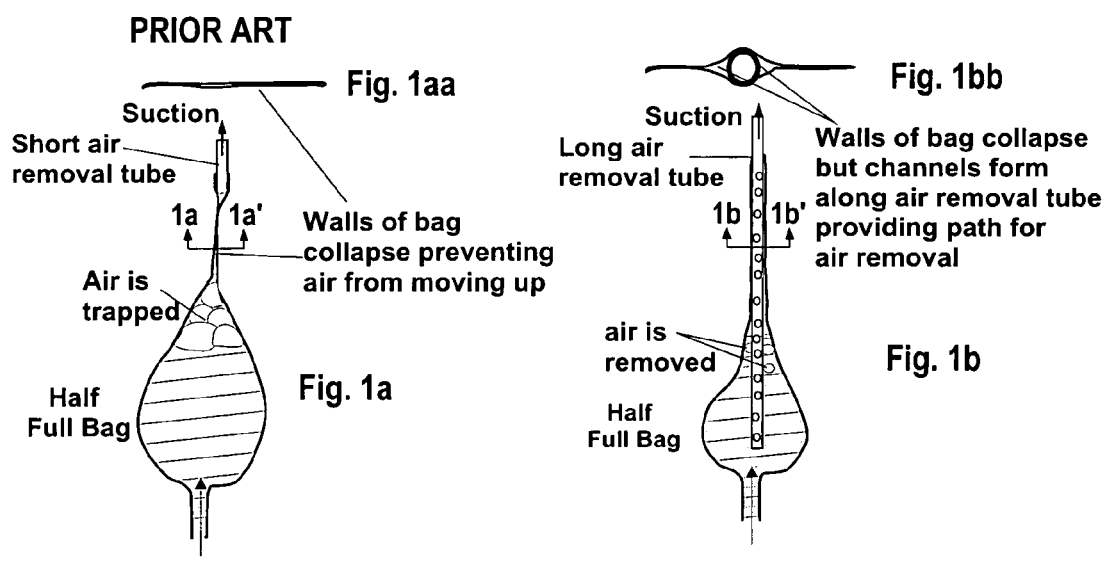
Fig. 1aa — Fig. 1a
Suction
Short air removal tube
1a   1a'
Walls of bag collapse preventing air from moving up
Air is trapped
Half Full Bag
Fig. 1bb — Fig. 1b
Suction
Long air removal tube
1b   1b'
Walls of bag collapse but channels form along air removal tube providing path for air removal
air is removed
Half Full Bag

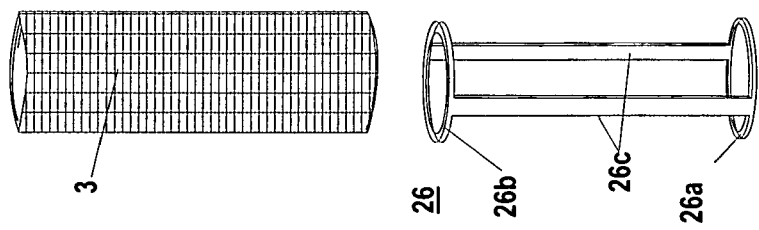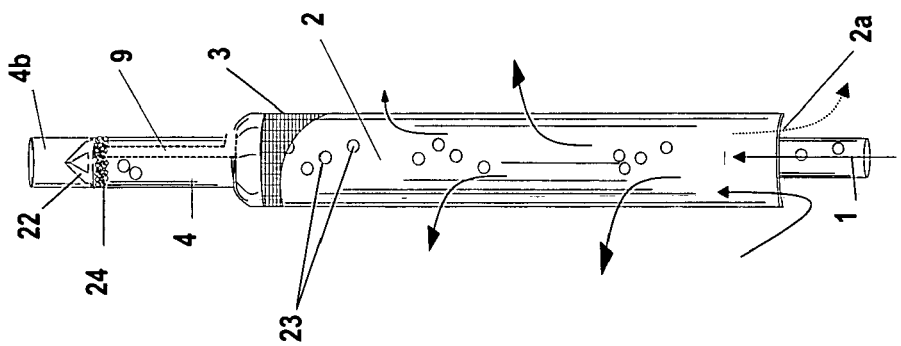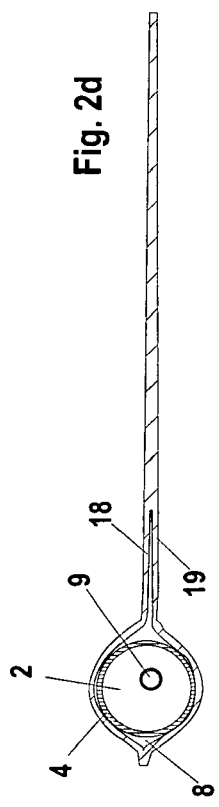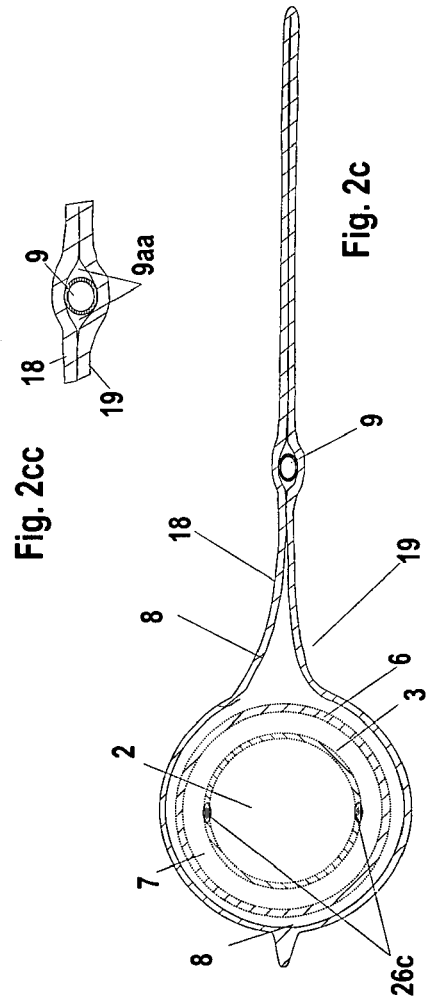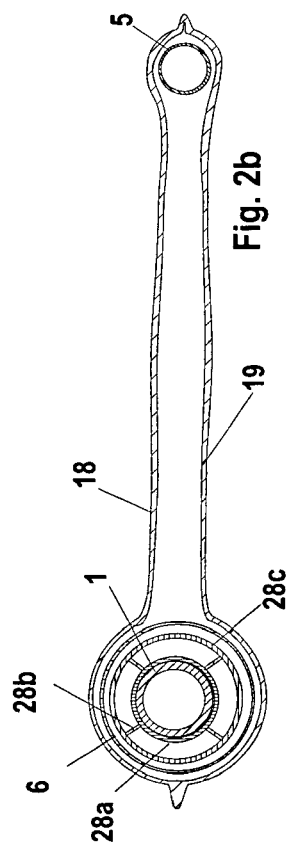

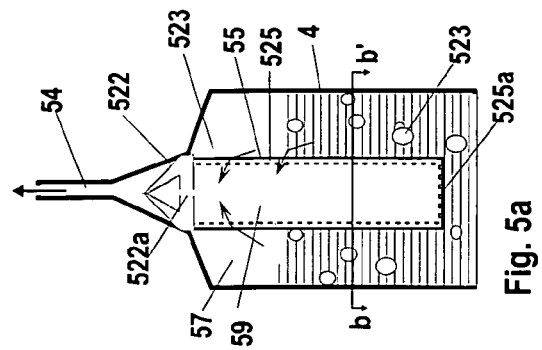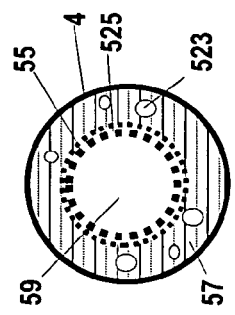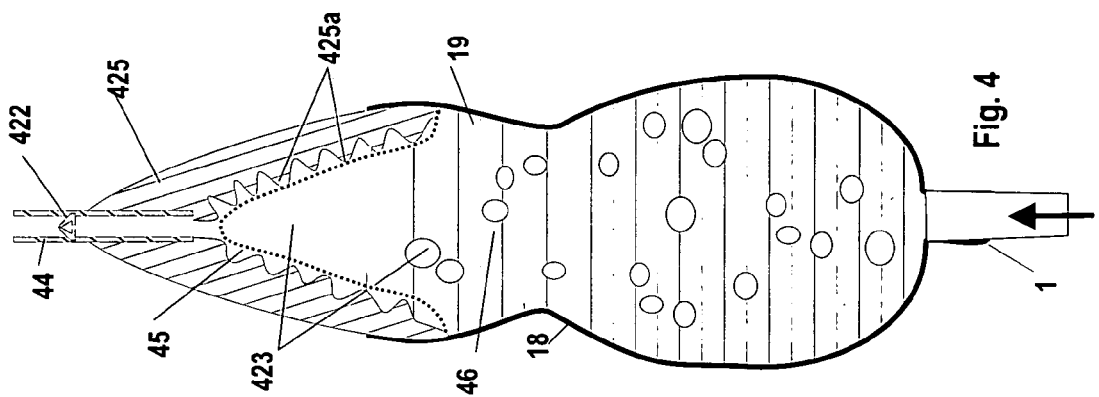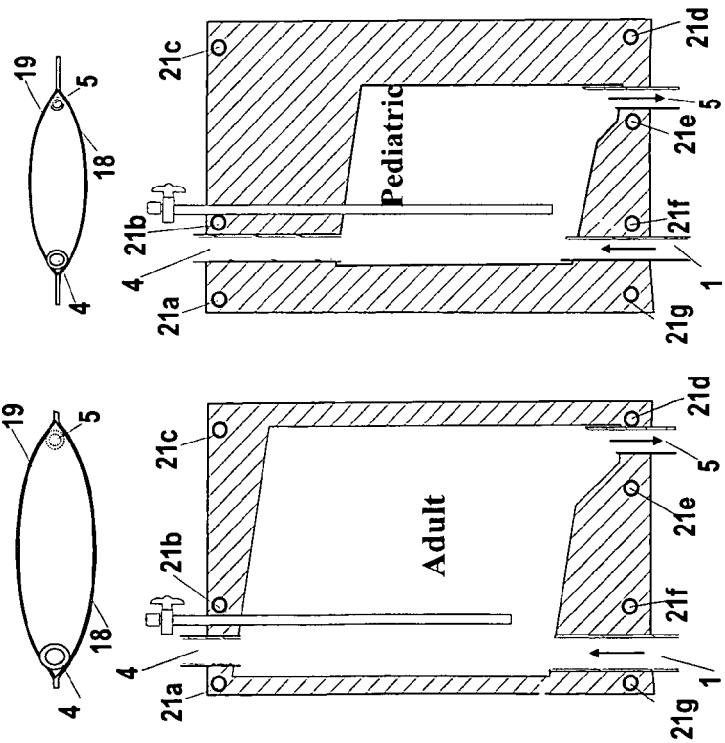

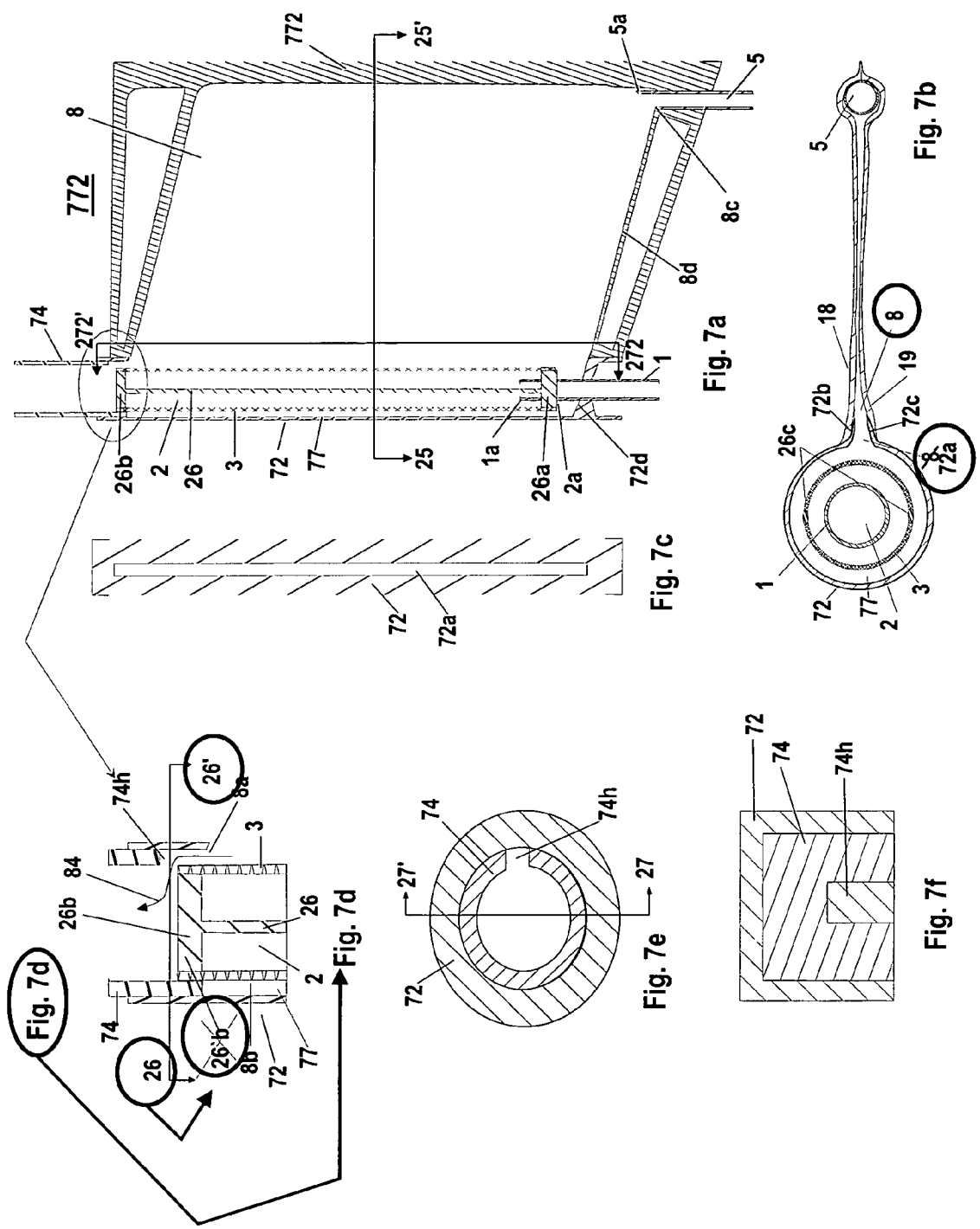

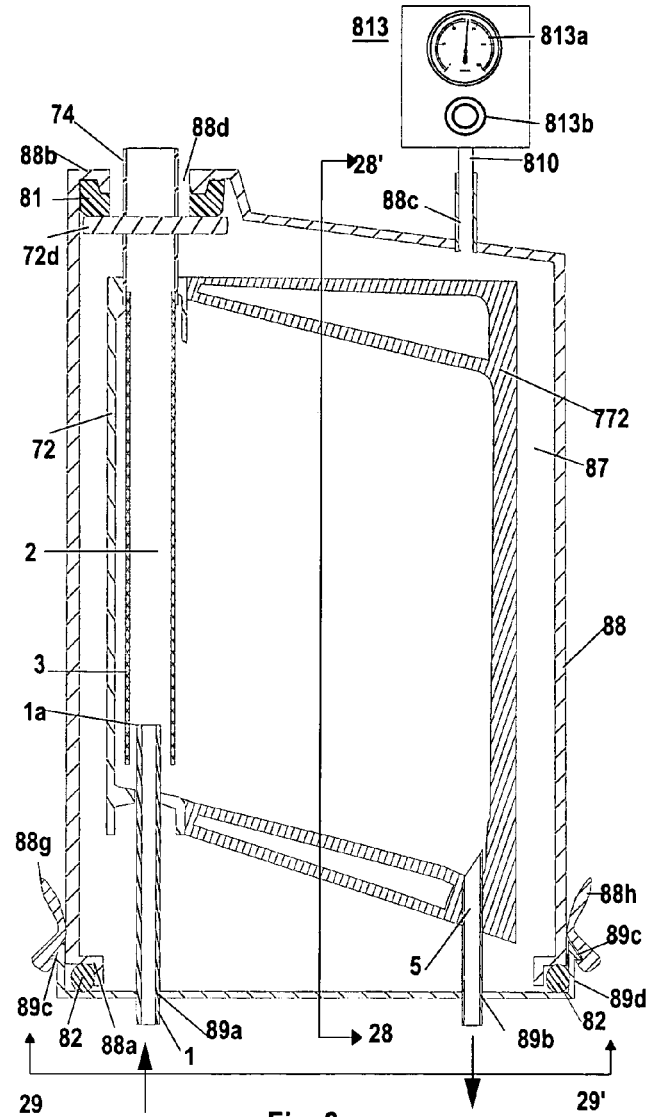
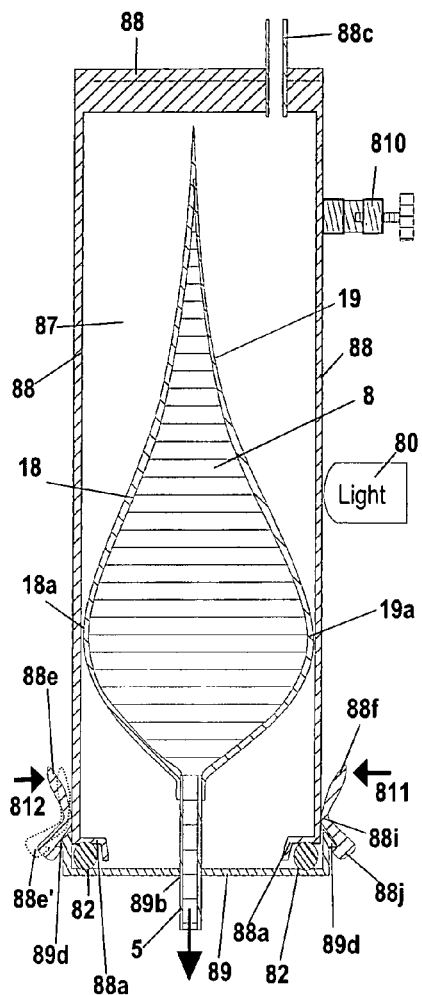
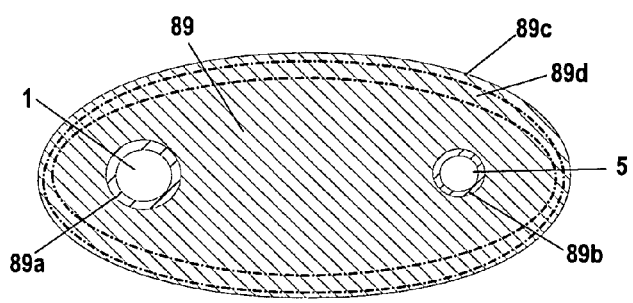
Fig. 8a
Fig. 8b
Fig. 8c

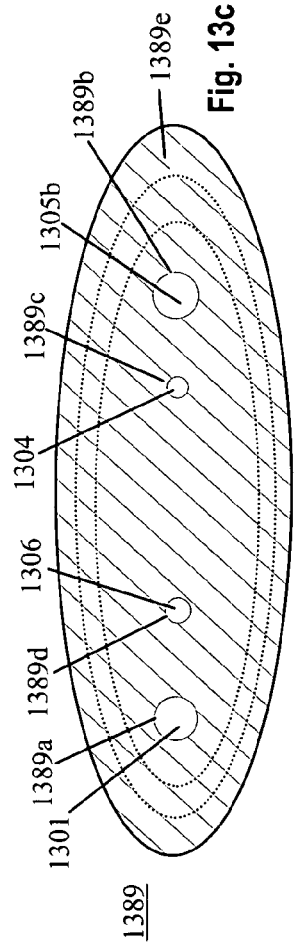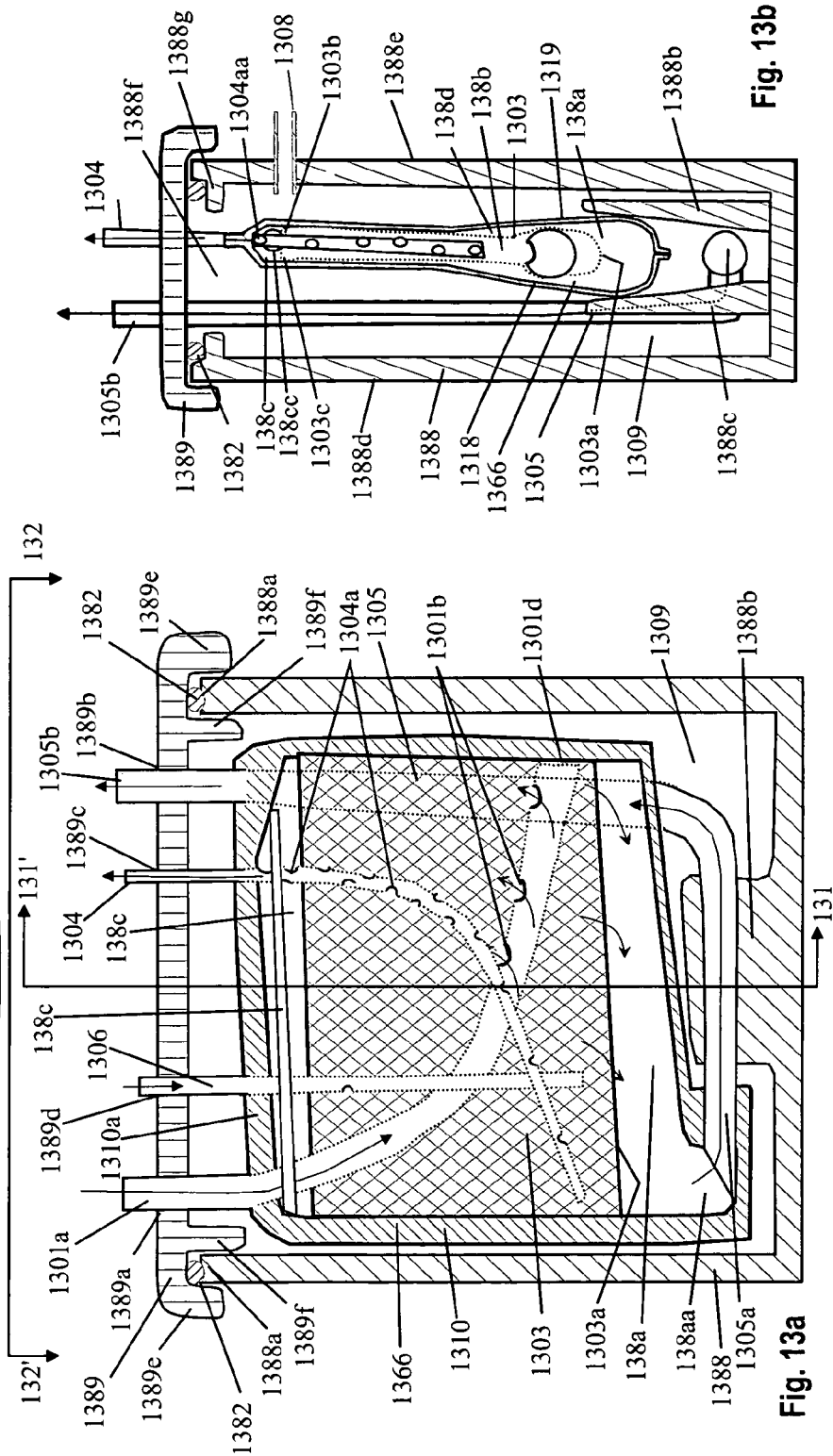

AUTOMATED MEANS TO REMOVE AIR FROM VENOUS BLOOD DURING CPB

CROSS-REFERENCE TO RELATED APPLICATIONS

This a divisional application of allowed U.S. application Ser. No. 09/795,782 filed Feb. 28, 2001, now U.S. Pat. No. 6,773,426 issued Aug. 10, 2004, application PCT/US99/19477 filed Aug. 30, 1999 (now published as WO012155A1: An Improved Soft Shell Venous Reservoir), and U.S. application Ser. No. 09/141,960 filed Aug. 28, 1998 now U.S. Pat. No. 6,337,049, the disclosures of these applications and patents being incorporated herein by reference thereto.

GOVERNMENT INTERESTS

This invention was in part made with government support under SBIR Grant #R44HL-55034 awarded by the National Institute Health, National Heart, Lung, and Blood Institute. As such the government may have certain rights in the invention.

BACKGROUND OF THE INVENTION

1. Field of the Invention

The invention is a blood reservoir with at least one pliable wall having at least three innovative features. First, the compliant reservoir is sealed within a rigid housing allowing control of the "atmospheric" pressure surrounding the bag, and therefore the pressure at which the bag would collapse. This first invention enables vacuum augmented venous drainage (VAVD) with a collapsible soft-shell reservoir (i.e. venous bag) and is particularly useful for cardiopulmonary bypass. Second, the invention incorporates means that improve gas bubble removal from blood transiting the collapsible reservoir. Third, a reservoir with all ports extending from its top is disclosed, an innovation that provides easy loading/unloading of the reservoir in/out of its holder and simplifies sealing the reservoir in a chamber thereby allowing the aforementioned VAVD.

2. Description of the Prior Art

Blood is routinely pumped outside the body during dialysis, cardiopulmonary bypass, and long-term cardiac and/or respiratory support (e.g. extracorporeal membrane oxygenation, ECMO). In general, blood flows from the venous side of the patient to a venous reservoir that is usually maintained at atmospheric pressure. Blood flow from the patient to the reservoir is a function of the resistance of the fluid conduit between patient and reservoir, and the pressure difference between patient and reservoir. When the reservoir is maintained at atmospheric pressure, that pressure difference is the height difference between patient and reservoir; the resulting flow is referred to as gravity drainage. Venous drainage by gravity alone provides inadequate return during procedures such as minimally invasive cardiac surgery and bypass via femoral cannulation. Usually it is the resistance of the venous cannula that limits the flow rate. Vacuum augmented venous drainage (VAVD) is a technique that overcomes flow limitations by applying suction to the hard shell reservoir thereby increasing the pressure difference between the venous cannulation site and venous reservoir. VAVD allows for a decrease in the inner diameter of the venous line, thereby reducing prime volume and enabling the use of a smaller cannula, which translates to an easier insertion, a better surgical view and a smaller surgical incision. This method precludes the use of the safer soft-shell closed venous reservoir (venous bag) unless a more expensive and complicated two-pump system is used (see McKusker K, Hoffman D, Maldarelli W, Toplitz S, and Sisto D. High-flow femoro-femoral bypass utilizing small cannulae and a centrifugal pump on the venous side, see Perfusion 1992; 7:295–300.

Clinically, a venous bag is used because it provides significant safety features. If the bag empties, it collapses, thereby preventing gross air from being pumped to the patient. It usually has no air-blood interface, and it requires no antifoam agents that can embolize into the blood. A recent study by Schonberger et al (Schonberger J P A M, Everts P A M, and Hoffmann J J. "Systemic blood activation with open and closed venous reservoirs. Annals of Thoracic Surgery, 1995; Vol. 59, pages 1549–55) comparing the hard shell to the bag reservoir found significantly lower blood activation, shed blood loss, crystalloid infusion, and hemolysis, and less donor blood infusion with the bag reservoir. Schonberger's group recommended against routine use of an open (hard shell) venous reservoir system. Currently, a slight negative pressure applied to the venous line (to facilitate blood drainage) using a single pump is possible with less desirable hard shell venous reservoirs. It is impossible to apply negative pressure to current soft-shell reservoirs, but it is possible with the present invention.

In an open, hard shell reservoir, air escapes by floating to the top of the reservoir. In a bag reservoir, air floats to the top but must be actively eliminated. This can be done manually with a syringe, or more frequently with a roller pump operating slowly so as to continuously pump fluid to the cardiotomy reservoir. With either method, a sudden large volume of air can overwhelm the air removal system and cause disastrous consequences, especially without a vigilant perfusionist. With one preferred embodiment of the present invention, air would be eliminated automatically without a roller pump or intervention by the perfusionist, and priming of the extracorporeal circuit would be facilitated through faster air removal utilizing either a floating ball valve or a hydrophobic membrane. Currently there are devices used in the CPB circuit that incorporate hydrophobic membranes that remove air yet do not allow blood to cross (e.g. Model # AutoVent-SV, Pall Corp Glen Cove N.Y.). Studies with filters used in these applications have shown that the membranes clear air from water almost indefinitely (many days), even if high suction is applied, without reducing gas transfer rate over time. However, when the membrane is exposed to blood, especially when high suction is applied, a film forms on the membrane over time, causing a significant increase in resistance to gas flow. The present invention incorporates designs and means to reduce this problem and extend the life of the membrane when used with blood. Likewise, U.S. Pat. No. 3,849,071 shows a floating ball within a blood filter that supposed to open a purge port when air enters and close when the blood level rises. However, as described, it is a physical impossibility for the ball to "fall" and open the purge port because, as shown, the weight of the floating ball is insufficient to overcome the force holding the ball against the purge port. With the present invention, the relative weight of the ball, the internal diameter of the purge port, and the suction applied to the purge port are designed to assure that the ball will drop to open the purge port in response to air level in the venous reservoir.

With prior art soft-shell reservoirs (SSR) air may be trapped at the top of the liquid by the collapsed walls of the reservoir, see FIG. 1a and 1aa. U.S. Pat. No. 4,622,032 illustrates a soft shell reservoir having an inlet tube extending from the bottom half way into the reservoir. This arrangement helps bubbles move up to the top of the extended tubes but the bubbles can still be trapped above said tubes. U.S. Pat. No. 5,573,526 illustrates the prior art soft-shell reservoir having its gas removal tubes (i.e. 18 and 20 of FIG. 1) extending from the top less 40% of the height of its blood chamber into the reservoir. All other prior art SSR have air removal tubes that are shorter with many having vent tubes that do not extend into the SSR at all (e.g. U.S. Pat. No. 5,580,349). As FIGS. 1*b* and 1*bb* illustrate, a tube extending from the top and into the SSR prevents complete collapse of the pliable walls of the bag thereby forming a pathway for air to move upward. The prior SSR air removal tubes extend less than 40% of the height of the blood chamber and therefore air still may be trapped below said tubes.

A soft shell venous reservoir sold by Medtronic Model # Maxima 1386 shows a soft shell reservoir with an inline tube extending, along one side of the bag, to the gas purge port at a 45° incline. This design has a rigid fluid path between blood inlet and gas purge port. However, this design is not as conducive to air removal as a vertical fluid path would be. In addition, the tube extending between inlet tube and purge port had an ID of ⅝", or only 25% greater diameter than the inlet tube. Thus, the velocity of the liquid in the column slows to only 64% of the inlet velocity. In another aspect of the present invention, a vertical path is provided from the blood inlet at the bottom of the bag to the gas purge port at the top of the bag, such path limiting the aforementioned problem of trapped air. The vertical path also has a large enough diameter that slows the velocity of the liquid to 25% or less of the inlet velocity. A lower blood velocity is more conducive to bubble removal.

State of the art soft shell venous reservoirs with a screen are designed such that a large portion of the screen contacts the internal walls of the bag, thereby increasing the resistance to blood flow across the screen, and rendering that portion of the screen ineffective, at least partially. This contact between the screen and the walls of the bag increases as the volume in the reservoir decreases. One aspect of the present invention reduces that problem by preventing the external walls of the venous reservoir from contacting the screen.

The indication of blood level in present soft shell venous reservoir is very inaccurate and low level, or air-in-the-reservoir, alarms are not reliable because many are designed for hard shell reservoirs. The present invention provides effective means to alarm at low blood levels and in the soft shell venous reservoir.

Currently, at the end of the bypass procedure, the patient is weaned off the heart lung machine by reducing the bypass flow. This is achieved by partially clamping the venous line and decreasing the speed of the arterial pump. Once off bypass, the blood left in the venous reservoir is gradually pumped back to the venous side of the patient. Another aspect of the invention allows the user to adjust the positive pressure applied to the blood within the venous reservoir. By being able to increase the pressure of the venous reservoir, the user can effectively reduce venous drainage or perfuse the blood back to the patient. This is not possible with current venous reservoir bags and may be dangerous with hard shell reservoirs (i.e., air may be pushed to the patient).

The inventor has also previously described an inline bladder (The Better-Bladder™, now U.S. Pat. No. 6,039,078), a device with a thin walled, sausage shaped bladder sealed inside a clear, rigid housing. Since the bladder is made from a single piece of tubing, the blood path is smooth with no flow discontinuities. The bladder portion is sealed within the housing that has an access port to the housing space outside the bladder. Because of its thin wall, the enlarged section can easily collapse. Thus, it can serve as an inline reservoir, providing compliance in the venous line to reduce the pressure pulsations at the pump inlet. The Better-Bladder also transmits the blood pressure flowing through it across its thin wall, allowing pump inlet pressure to be measured noninvasively by measuring the gas pressure of the housing via the gas port. The degree of "gravity drainage" is user-adjustable by setting the negative pressure in the Better-Bladder housing. If the suction generated by the venous pump becomes too great, the pump is slowed or stopped by a pump controller. The Better-Bladder does not have a gas purge port or a screen to inhibit gas bubbles. It is also much smaller, having nominal volume of 80 ml for adult perfusion as compared to over 1,000 ml for a venous reservoir.

Despite users acknowledgement that SSR are safer, hard shell reservoirs are easier to use and therefore more widely used. For example, it is easier to connect the inlet tubing located at the top of the hard shell reservoir than to the inlet tube of the SSR located at the bottom. Though some SSRs are premounted by the manufacture to a supporting plate (e.g. Cobe see U.S. Pat. No. 5,693,039), most require multiple hanging hooks for proper support (e.g. Baxter's SSR model # BMR1900 has 3 holes at the top and 4 holes at the bottom), an inconvenience at best, a danger in an emergency. Present mounted SSR do not improve the tube connection by much. It would be a clinical advantage to provide a SSR that allows fast mounting and dismounting, and tube connection that are easy or even easier than that of hard shell reservoir. Another requirement for present SSR is the use of a supporting faceplate (e.g. see FIG. 3 of U.S. Pat. No. 5,573,526). These are used to improve the bubble path from the blood to the top of the reservoir. Such faceplates are again inconvenient, require additional assembly time by the user, and may obstruct the direct approach to the front wall of the bag. The latter is useful when bubbles "stuck" on the wall are to be dislodged. The elimination, or at least the reduced requirement, of a front plate is another desirable attribute.

U.S. Pat. No. 5,823,045 "Measuring Blood Volume in Soft-Shell Venous Resevoirs (sp.) by Displacement" illustrates a SSR enclosed in a rigid housing. This invention suggests sealing a SSR within a rigid housing but does not suggest applying vacuum to the fluid surrounding the SSR. In fact, neither the FIGs. nor the specifications mention a port for adjusting the fluid in sealed container 12. Van Driel's patent has some major flaws. The tubes connected to the bag are to be "threaded through resilient seals 26 in the bottom of container 12 . . . " also renders '045 clinically irrelevant. If, though not described as such, container 12 is disposable, then the system as described is too expensive. If, as understood, container 12 were not disposable, then "threading" the tubes would break sterility, and would be very difficult, especially if a seal is required. Further, since the outside diameter of perfusion connectors are larger than the OD of the tubing they connect, it would be impossible to have any of the tubing of the SSR connected to anything until after they have been threaded. In addition, the housing needs to be sufficiently wide for the user to place their hands and thread the inlet and outlet tubes at the bottom of box 12, a major disadvantage that hinders quick setup and increases the likelihood of contamination. This invention has not been reduced to clinical practice.

Since the SSR is sealed in container 12, external means are provided by '045 to "massage" the SSR with "vibrator" 36. In fact, since vibrator 36 is not connected to the wall of the SSR, it can only squeeze the wall rather than the pull and push motions required for vibration. This provides significantly less manipulation ability as compared to direct contact with the bag.

PCT's International Publication Number WO 99/08734 entitled "System and Method for Minimally Invasive Surgery Vacuum-Assisted Venous Drainage" illustrates in FIG. 9 a standard SSR ("preferably BMR-800 or BMR-1900") completely sealed in a rigid housing. It is also suggested that " . . . a pressure differential between the interior and exterior of the reservoir . . . " be maintained. This design is as impractical as that of US Pat, '045. If the bag and rigid housing are assembled and shipped to the end user as a single unit, the unit becomes very expensive and therefore would be used only for VADV cases. The expense arises from a housing required to support a large force. The force can be calculated as (Pressure)*(Area). Thus, to support a pressure of −250 mmHg with a safety factor of 2 for a box that holds a bag like the BMR-1900 (10" high by 12" wide), the force on each faceplate is 1200 lb! The inventors did not suggest, nor showed or described, a mechanism for the user to seal the bag in the box. Even if there was a mechanism, it would be very difficult, time consuming, and, as described with relation to '045, most likely to break sterility. And, once sealed it would be impossible for the user to contact the bag.

Both '045 and '08734 illustrate the rigid housing as a rectangular box. A better design to support the large external force due to the large area and vacuum used would be an ellipsoid cross section or at least rounded corners.

Both '045 and '08734 illustrate the great need for designs that allow simple, inexpensive, and quick means to seal and remove the bag from its container even with long tubing or large connectors without affecting its sterility. Simple and quick means to reach the enclosed bag would also be welcomed. The present invention overcomes these clinically non-workable prior art designs.

It is standard practice to place the venous reservoir above the oxygenator to assure that the microporous membrane is always under positive pressure. A negative pressure would result in air crossing the membrane and entering the arterial line, a very dangerous situation. When VAVD is used, suction can be applied to the venous reservoir only once the arterial pump is generating a positive pressure in the arterial line. Otherwise, the suction applied to the venous reservoir can draw air across the membrane. A one-way valve at the pump outlet prevents vacuum applied to the venous reservoir from reaching the membrane oxygenator, but a one-way valve incorporated into the outlet of the present venous reservoir is preferable. Means to assure that the gas side of the membrane oxygenator is always positive relative to the blood side would also be a major safety feature for all VAVD applications.

BRIEF SUMMARY OF THE INVENTION

The present invention incorporates improved designs for venous reservoirs that provide the benefits of prior art devices (limiting pump suction using the safer, pliable blood reservoir) while avoiding their disadvantages (air entrapment, inability to utilize VAVD, required vigilance for air removal). Further, its advantages and uniqueness are also enhanced by providing the user with means to adjust the degree of suction applied for venous augmentation and assuring that a greater area of the screen is effective in liquid transport.

Briefly, the present invention in its simplest form consists of a blood reservoir having at least one pliable wall, a blood inlet, a blood outlet, and a gas purge port. In one preferred embodiment, a first structure having tubular cross section and semirigid wall is placed above said inlet thereby providing a first path for undesirable bubbles entering the reservoir to move to the top where they are eliminated via said gas purge port. The first structure preferably has an effective cross section that is larger than the ID of said inlet tube thereby slowing any blood flow and allowing more favorable conditions (longer time, lower drag) for gas bubbles to float upward. The wall of the first structure is sufficiently rigid to prevent collapse of said pliable wall from blocking said first path. In another preferred embodiment, the pliable wall of the venous reservoir is sealed externally, forming a pressure chamber external to the venous reservoir. Controlled suction applied to said external chamber is transmitted across said pliable wall thereby controlling the negative pressure of the blood at which said pliable wall moves.

Another preferred embodiment has all the tubes at the top of the SSR. These tubes pass through, sealed within, and physically supported by a rigid disposable supporting plate providing three major advantages. First, the bag is supported by hanging the supporting plate in a supporting fixture, much like the hard shell reservoir. This allows the user to "drop in" the SSR and just as easily remove the SSR from its holder. Second, the supporting plate provides simple sealing means along a single plane, an extremely important feature for simple and secure sealing of the SSR within housing for VAVD applications. Third, by having all the tubes for the bag entering from its top, the bottom of the bag is unhindered and can be placed lower to the floor allowing greater gravity drainage. In addition, because the bag hangs from the top, the weight of the SSR/blood contributes to the seal of the supporting plate against the housing. Designed properly, this gravitational force can eliminate or greatly simplify any clamping required by other designs.

It is therefore the objective of the present invention to provide an improved venous blood reservoir with at least one pliable wall that provides a path for gas bubbles entering the inlet to move unhindered up to the gas purge port.

A further objective of the present invention is an improved venous blood reservoir, having at least one pliable wall, allowing the user to adjust the negative pressure applied to said pliable wall thereby allowing for augmented venous drainage.

A further objective of the present invention is an improved venous blood reservoir designed to maintain its external wall from contacting the screen material and thereby reducing the resistance to blood flow across the screen.

Yet another objective of the present invention is to incorporate a one-way valve at the outlet of the venous reservoir, said valve preventing blood from being sucked into the venous reservoir when pressure at the outlet of the venous reservoir is positive relative to the liquid pressure in the venous reservoir.

Another objective of the present invention is to provide an improved venous blood reservoir with at least one pliable wall that when placed at the pump inlet, provides compliance that reduces pressure fluctuations at said pump inlet.

Another objective of the present invention is to provide an improved venous blood reservoir with at least one pliable wall that when placed at the pump inlet, provides automated means to eliminate air.

Another objective of the present invention is to provide an improved venous blood reservoir with at least one pliable wall and with a relatively large gas purge port, said port providing a more volumetrically effective gas purge, and one that is less traumatic to the blood.

Another objective of the present invention is to provide automated means to detect air in the venous reservoir and utilize said means to alarm the user or control the suction used to remove air from the venous reservoir.

Another objective of the present invention is to provide the user with a SSR that is simple to use, and easy to load and unload from its holder or from its container.

Another objective of the present invention is to provide the user with a SSR having all its connections above the bag facilitating said connections and allowing a lower placement of the reservoir thus providing greater gravity drainage.

Another objective of the present invention is to utilize gravity to facilitate sealing of the SSR in its VAVD container.

Another objective of the present invention is to utilize the applied suction to facilitate sealing the SSR within its VAVD container.

Another objective of the present invention is to provide a single plane to seal SSR in VAVD container.

Another objective of the present invention is to provide a non-disposable VAVD container that supports at least −100 mmHg.

Another objective of the present invention is to provide a disposable cover/holder as part of the SSR for the VAVD container.

Yet another objective of the present invention is to provide a single venous bag that can be used with either standard or with VAVD thus, reducing cost of inventory and simplifying the user's set up.

Another objective of the present invention is to provide a disposable SSR incorporating a structure that facilitates sealing the bag within a non-disposable VAVD container, thus reducing cost.

Another objective of the present invention is to provide a SSR incorporating means to prevent the SSR from pulling out of, or twisting within its holder.

Another objective of the present invention is to provide a means to allow suction application to both SSR and cardiotomy independent of the height difference between the two.

Another objective of the present invention is to provide a means to reduce the chance of gas pulled across the microporous membrane when suction is applied to the venous reservoir.

Another objective of the present invention is to provide a VAVD housing having an ellipsoid cross section that can better support a large external force and streamlined to the shape of the SSR.

Another objective of the present invention is to provide a VAVD housing for SSR that does not require the user's hands to be placed within said housing when mounting said SSR in said housing Other objectives, features and advantages of the present invention will become apparent by reference to the following detailed description, but nonetheless illustrative, of the presently preferred embodiments thereof with reference to the accompanying drawings therein.

BRIEF DESCRIPTION OF THE DRAWINGS

FIG. 1 is a line drawing of the pertinent components of a typical cardiopulmonary bypass (CPB) circuit showing the relative location of the venous reservoir of the present invention.

FIG. 1a is a line drawing of a typical prior art venous reservoir illustrating how incoming air bubbles are prevented from reaching the gas exhaust port and are trapped midway in the bag.

FIG. 1aa is a line drawing of a cross section taken of FIG. 1a along line 1a–1a'.

FIG. 1b is a line drawing of a typical venous reservoir according to the present invention, illustrating a pathway provided by channels formed along a tube extended into bag.

FIG. 1bb is a line drawing of a cross section taken of FIG. 1b along line 1b–1b'.

FIG. 2b is a line drawing of a cross section taken of FIG. 2a along line 15–15'.

FIG. 2c is a line drawing of a cross section taken of FIG. 2a along line 16–16'.

FIG. 2cc is an enlarged view of the circled section taken from FIG. 2c.

FIG. 2d is a line drawing of a cross section taken of FIG. 2a along line 17–17'.

FIG. 2e is a line drawing illustrating the flow of blood and air at the inlet of the venous reservoir shown in FIG. 2a.

FIG. 2f is a line drawing illustrating one preferred method to assemble the screen used with the venous reservoir shown in FIG. 2a.

FIG. 3a is a line drawing illustrating one preferred sealing scheme of an adult size venous reservoir that allows the use of a universal holder for it and the pediatric venous reservoir shown in FIG. 3b.

FIG. 3b is a line drawing illustrating one preferred sealing scheme of a pediatric size venous reservoir that allows the use a universal holder for it and the adult venous reservoir shown in FIG. 3a.

FIG. 4 is a line drawing illustrating one preferred embodiment of the present invention where the venous reservoir is topped with a microporous membrane that allows air, but not blood, to be removed.

FIG. 5a is a line drawing illustrating another preferred embodiment of a microporous membrane placed at the top of the venous reservoir allowing air, but not blood, to be removed.

FIG. 5b is a line drawing of a cross section taken of FIG. 5a along line b–b'.

FIG. 7a is a line drawing illustrating another preferred embodiment of the present invention where a rigid cylinder, incorporated as one external wall of the venous reservoir, maintains the screen wall unhindered and provides an uninterrupted fluid path between blood inlet and gas exhaust port.

FIG. 7b is a line drawing of a cross section taken of FIG. 7a along line 25–25'.

FIG. 7c illustrates rigid cylinder 72, shown in FIG. 7a, isolated and rotated 90° clockwise.

FIG. 7d is an enlarged view of the top, circled section of the venous reservoir shown in FIG. 7a illustrating the slot providing communication for removal of air external to the screen.

FIG. 7e is a line drawing of a cross section taken of FIG. 7d taken along line 26–26'.

FIG. 7f is a line drawing of a cross section taken of FIG. 7e taken along line 27–27'.

FIG. 8a is a line drawing illustrating one preferred embodiment of the present invention where a venous reservoir can be sealed within a rigid housing where suction can be applied to the external flexible walls of said reservoir thereby providing venous augmentation.

FIG. 8b is a line drawing of a cross section taken of FIG. 8a along line 28–28'.

FIG. 8c is a line drawing of a cross section taken of FIG. 8a along line 29–29' illustrating the rigid bottom cap used with the venous reservoir to seal the bottom of the housing shown in FIG. 8a.

FIG. 9b is a line drawing of a cross section taken of FIG. 9a along line 30–30' showing the bottom seal of the venous reservoir within the housing and door shown in FIG. 9a.

FIG. 9c is a line drawing of a cross section taken of FIG. 9a along line 31–31' showing the top seal of the venous reservoir within the housing and door shown in FIG. 9a.

FIG. 9d is a line drawing of a cross section taken of FIG. 9a along line 32–32' showing another preferred sealing means incorporated into the inlet tube of the venous reservoir shown in FIG. 9a.

FIG. 9e is a line drawing of a cross section taken of FIG. 9d along line 33–33' showing a top view of the means incorporated into the inlet tube of the venous reservoir shown in FIG. 9a.

FIG. 10b is a line drawing of a longitudinal cross sectional view of FIG. 10a.

FIG. 10c is a line drawing of a cross section taken of FIG. 10b along line 10c–10c' showing another view of the venous reservoir within the housing shown in FIG. 10a.

FIG. 13a is a line drawing illustrating one preferred embodiment of the present invention where all the tubes entering the bag enter from the top and are supported by a disposable supporting plate.

FIG. 13b is a line drawing of a cross section taken of FIG. 13a along line 131–131'.

FIG. 13c is line drawing of a cross section taken of a top view of cover 1389 of FIG. 13a along line 132–132'.

FIG. 13dd is a line drawing of a cross section taken of FIG. 13d along line 133–133'.

FIG. 13ee is a line drawing of a cross section taken of FIG. 13e along line 134–134'.

DETAILED DESCRIPTION OF THE INVENTION

Figure 2A:
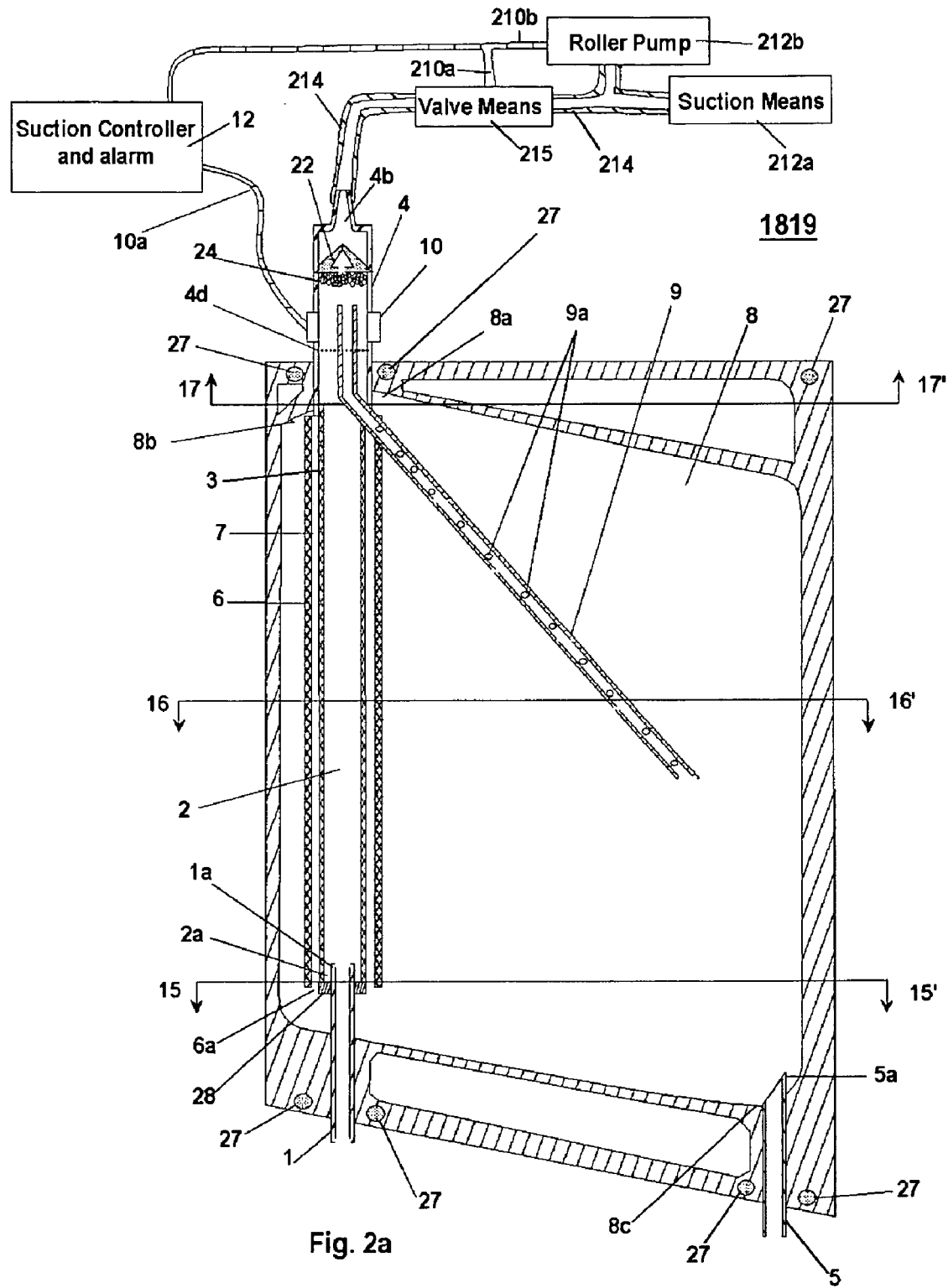
FIG. 2a is a line drawing illustrating one preferred embodiment of the present invention where a perforated cylinder is used to keep the flexible walls of the venous reservoir bag away from its screen as well as provide an uninterrupted fluid path between blood inlet and gas exhaust port. Also shown are automated means to remove air from the venous blood.

Reference should now be made to the drawings wherein the same reference numerals are used throughout to designate the same or similar parts. It should be noted that the use of cardiopulmonary bypass, as shown in FIG. 1, is for descriptive purposes, and should not be taken as a limitation to the use of the devices described hereinafter. It should also be noted that the term soft shell reservoir, venous bag and bag are used interchangeably.

FIG. 1 is a schematic representation of a system according to the present invention and showing the relative location of the venous reservoir in a typical cardiopulmonary bypass circuit. As shown, tubing 123 is inserted at one end by means of a cannula (not shown) in the vena cavae for obtaining venous blood from the heart (not shown) of patient 1102. Tubing 123 is coupled, as an example, to venous reservoir 1103. The blood is drawn from venous reservoir 1103 via tube 135 by roller pump 1104 and pumped through a membrane oxygenator 1105 wherein oxygen is supplied to the blood and carbon dioxide is removed. The blood from the oxygenator is then conducted by means of tubing 157 to arterial filter 1107 and then via tubing 172 and an arterial cannula (not shown) back to the patient. As described in the prior art, the venous blood, here shown coming from the patient's vena cavae, may contain air that must be eliminated before it is pumped back to the patient. This is one of the main functions of the venous reservoir. As shown, air entering venous reservoir 1103 rises to the top of said reservoir where it is removed by suction pump 1114 to cardiotomy reservoir 1115. Roller pump 1104 is usually one of 3 to five pumps composing a heart-lung machine, which is part of a hardware required for cardiopulmonary bypass.

FIGS. 2a, 2b, 2c, 2d and 2e illustrate line drawings of one preferred embodiment of the present invention. Here, venous blood enters the venous reservoir 1819 via inlet tube 1 and is directed into first inlet chamber 2, shown as a cutaway. First inlet chamber 2 preferably has a circular cross section with its walls formed of fine screen 3 typically having a pore size of 40μ to 150μ and having an effective open area that is preferably greater than 40%. It is understood that though lower pore sizes result in higher resistance to blood flow, they prevent smaller bubbles from crossing the screen. It should also be understood that screen 3 is preferably heparin coated, to increase wettability and reduce clot formation. The top of chamber 2 is in fluid communication with gas purge port 4. The bottom of chamber 2 is open and is in fluid communication with inlet tube 1 and, via expandable chamber 8, with outlet tube 5. Preferably outlet tube 5 is located on the opposite side of, and lower than, inlet tube 1.

In one of the preferred embodiment, shown in FIG. 2a, first inlet chamber 2 has a larger inside diameter than inlet tube 1 (e.g. 1.0" v. 0.5"), said larger diameter serves to slow the velocity of the blood (e.g. ¼ the inlet velocity), and thus allow more time for bubbles to rise to the top where they can be removed. Slowing the blood also reduces the tendency of the flowing blood to carry the bubbles, especially the smaller ones, by reducing the drag on the bubbles by the moving blood. Lower velocity also lowers the tendency of larger bubbles to break into smaller ones; larger bubbles have a higher buoyancy and less of a chance of crossing screen 3 into expandable chamber 8, and flowing out of the bag through outlet tube 5 shown in FIG. 2a. With sufficient pressure across screen 3, the bubbles could cross into chamber 8 and travel to outlet 5 of the reservoir, a very undesirable outcome. To reduce that possibility, inlet chamber 2 is open at the bottom where debubbled blood can exit first inlet chamber 2 at 2a. To improve flow conditions, the outlet of inlet tube 1, 1a, is preferably centered with the centerline of chamber 2, as also shown in FIG. 2b (cross-section 15–15' in FIG. 2a). Also shown is one preferred embodiment of structure 28 that centers inlet tube 1 within chamber 2 formed by screen 3. Connector 28, shown in FIG. 2a and as a cross section taken of FIG. 2a along line 15–15' shown in FIG. 2b, lines up and connects inlet tube 1 to inlet chamber 2. Thus, in one preferred embodiment, connector 28 has a wheel cross-section with an internal circular structure 28a connected via spokes 28b to an external circular structure 28c. The inside diameter of inside structure 28a that allows interference fitting to the outside diameter of inlet tube 1 and the outside diameter of outside structure 28c supports cylinder 6. The space between internal structure 28a and outside structure 28c maintained by spokes 28b forms a fluid communication between inlet chamber 2 and expandable chamber 8 as indicated by the downward facing arrow at the bottom of FIG. 2e. It should also be obvious that since screen 3 may be flimsy, it may need radial support, as for example internal cage 26, see FIG. 2c (cross section 16–16' in FIG. 2a) and 2f. Screen 3 can be attached to cage 26 by various means (e.g. insert molding) longitudinally and radially to 26a or 26b and longitudinally to ribs 26c, for example, by adhesive. This would maximize the ID of first internal chamber 2 to provide a smooth and straight vertical flow path thereby facilitating the upward motion of the bubbles.

With this design, as is the case for present venous reservoir bags (e.g. Bentley, Cobe, Sarns/3M, Minntech) most of the incoming blood would exit via screen 3 across which very few bubbles, if any, cross. However, present venous reservoir bags are made of four layers: the two outside layers being flexible PVC sheets and the two inside layers being a screen (e.g. U.S. Pat. No. 4,734,269). The screen is usually folded over with the fold being in the center of the venous reservoir bag and its edges sandwiched and sealed along at least two of edges of the two PVC outer layers. This design is simple but it provides no means to keep the internal surface of the external PVC walls from contacting the external wall of the screen. This contact reduces the effective screen area available for blood flow, especially at low blood volumes, causing further problems because more bubbles cross the screen at lower blood volumes. For example, tests conducted with the Cobe venous reservoir bag (Model # VRB, Cobe Lakewood, Colo.) showed that at a blood flow of 4.0 L/min and an air flow of 750 mL/min, the bubble count (size >50μ) with a blood volume of 750 ml in the bag was 35 bubbles/sec as compared to 94 bubbles/sec when the blood volume was 500 ml. The Baxter venous reservoir bag (Model # BMR-1900, Baxter/Bentley Irvine, Calif.) had similar results: the bubble count increased from 69 bubbles/sec to 160 bubbles/sec when the blood volume decreased from 750 to 500 ml.

The present invention eliminates the problem of screen to wall contact by introducing means to maintain the wall of the venous reservoir bag away from the screen as well as to maintain a vertical column of blood within first inlet chamber 2. This can be achieved by either incorporating the means into the disposable bag, or by interfacing a disposable bag with a nondisposable holder, the combination providing the aforementioned means. FIG. 2a illustrates one preferred embodiment of the disposable type. Here, a semi rigid cylinder 6 with perforated wall is placed over screen 3 forming second inlet chamber 7 in fluid communication with expandable chamber 8 via said perforations as well as its open bottom at 6a. The perforations can be effectively formed by using a tubular net with, for example 0.030" to 0.100" diameter strands forming a diamond shaped opening, see 6 in FIG. 2a, and can be obtained from Nalle Plastics Inc. Austin, Tex. The tubular net can be made of polypropylene, polyester, Nylon, or polyethylene. It must possess at least three properties: 1) sufficient stiffness (either by rigidity of the material or thickness of the yarn) and structure to keep walls 18 and 19 (FIGS. 2b, 2c, 2d) of venous reservoir bag 1819 (FIG. 2a) away from screen 3 thereby maintaining chamber 7; 2) an opening to allow unhindered fluid communication between chamber 7 and expandable chamber 8; and 3) cause no undesired interaction with biological fluids. Tubular net 6 preferably extends vertically from the bottom of venous reservoir 1819 at its inlet to the top of said reservoir and can be attached to the external wall of air-venting tube 4 for support. The inlet to cylinder 6, 6a, may extend below screen 3 providing free fluid communication between inlet 1 and expandable chamber 8. With this design, experiments similar to those described for the Cobe and Baxter bags result in a steady bubble count of 60 at bag volumes of 500 and 1000 ml.

FIG. 2e illustrates the blood path of the present invention. Venous blood with some gas bubbles 23 enters the venous reservoir via inlet tube 1. The inertial forces of the blood exiting outlet of tube 1 propel the blood and bubbles upward into first inlet chamber 2. Chamber 2 is preferentially lined up within ±15° of the vertical line. This essentially vertical position, unlike prior art devices, provides the least resistance for gas bubbles to rise up chamber 2 to air-venting tube 4 where they are evacuated by suction applied to the outlet of tube 4, port 4*b*.

As shown in FIG. 2*a*, screen 3 extends to the top of venous reservoir 1819 where it is sealed to gas venting tube 4. This seal prevents blood from exiting at the top where it may drag bubbles out of inlet chamber 2 into expandable chamber 8. Should gas volume increase at tube 4 and displace blood volume at the top of chamber 2, the gas could cross screen 3 and enter chamber 7 and chamber 8. Because screen wall 3 may get wet again before all the gas at the top of chamber 8 is removed, that gas can be trapped. Purge tube 9 (see FIGS. 2*a* and 2*e*) is provided to allow gas to be purged from chambers 7 and 8. For that purpose, the topmost entry point of tube 9 into chamber 8 is the highest point in chamber 8 (e.g. point 8*a* is higher than point 8*b*). Tube 9 extends from air-venting tube 4 into chamber 8, said extension preferably having holes 9*a* in its wall to provide better fluid communication with chamber 8 along the entire length of tube 9. Holes 9*a* allows air to enter tube 9 and be evacuated as described before. Other holes may be punched into tube 9 to allow air to be evacuated at any blood level. The smaller diameter of tube 9 and the location of its outlet at the top of venting tube 4 reduces the chance of blood flowing (with bubbles) from chamber 2 to chamber 8 via tube 9. The extension of tube 9 into chamber 8 also forms two channels, shown as 9*aa* in FIG. 2 cc, for air to travel along the tube upwards because the tube prohibits the opposite walls of the bag from making complete contact. Channels 9*aa* increase in size with increasing outside diameter of air removal tube 9 and thicker/stiffer walls 18 and 19 of bag 1819. FIG. 1*b* and its associated view along 1*b*–1*b*', FIG. 1*bb*, illustrate how the present invention provides air channels. FIG. 1*a* and its associated view along 1*a*–1*a*', 1*aa* illustrate how prior art shorter air removal tube (e.g. prior art U.S. Pat. No. 5,573,526 FIG. 1 tubes 18 and 20) lack such channels. Tube 9 extends downward into blood chamber 8 at least 40% but preferably over 50% of the height blood chamber 8. As well known in the art, tube 9 can alternatively be sealed directly into chamber 8 and external to tube 4. As shown, tube 9 is exposed to the same suction applied to air-venting tube 4.

With the present invention because, air moves freely to the top of bag 1819 where it can be purged easily. It therefore should be obvious that the degree of suction applied and the blood volume removed in order to purge the gas should be significantly lower than with present devices. The smaller blood volume removed, the lower flow required to remove the gas and the larger ID of the purge line all contribute to significantly lower blood damage. This is especially true when stopcocks, which have a very small ID (e.g., 0.062" and sometimes less) and are used with present devices, are eliminated.

The user may not easily determine the presence of bubbles or the blood level in first inlet chamber 2 due to the opacity of the blood and/or screen 3. Yet another innovation provides means to easily ascertain the presence of bubbles by increasing the ID of air-venting tube 4 to at least ¼" but preferably ⅜" or greater. Other venous reservoir bags have gas ports of ⅛" ID or smaller, which presents a high resistance to gas and blood flow. The increased port diameter of the present invention increases the ease by which bubbles rise up tube 4 for two reasons. First, gas bubbles move up easier in a liquid filled tube having a diameter larger than the diameter of the bubbles. Second, a larger diameter tube accommodates larger bubbles with greater buoyancy, providing greater upward force on the bubbles relative to the capillary force within a liquid filled tube that inhibits their movement. Thus, by having an exhaust tube with a larger diameter, the user could pull blood up into tube 4. Should air enter first inlet chamber 2, it would travel up and replace the blood in tube 4 causing the visible blood level 4*d* (see FIG. 2*a*) in tube 4 to drop, an indication that air entered the venous reservoir and must be removed. It should be understood that the process can be automated by incorporating level detector 10 radial to tube 4, said detector 10 connected to a suction controller and/or alarm monitor via transmitter line 10*a*.

As shown, detector 10 provides means to detect the presence of air. Monitor/controller 12 provides means to alarm the user to air entering tube 4 and/or start a suction means that applies the required suction to outlet 4*b* of tube 4, to remove said air and raise the liquid level. Once the level detector detects the rising liquid (i.e. the absence of air), it stops the alarm and/or stops the suction used to remove the gas from the venous reservoir. Stopping air removal when the blood reaches the level of detector 10 assures that air but not blood is withdrawn from tube 4. Monitor/controller 12 can, for example, control suction means 212*b*, a roller pump, or valve means 215, via interconnecting means 210*a* or 210*b* respectively. When roller pump 212*b* is used as the suction means to removes the air from tube 4 via tube 214, and then the suction is controlled by controlling the speed of the pump. Alternatively, suction means can be wall suction (with or without a vacuum regulator). Here, the vacuum required to remove the air from tube 4 is controlled by control unit 12 actuating valve means 215 via interconnecting means 210*a*. The valve can open or close tube 214 interconnecting outlet 4*b* of tube 4 to suction means 212 by actuating valve means 215 that can for example, be a solenoid actuated tubing clamp that opens (unclamps) and closes (clamps) tube 214. Also, as described in reference to one way valve 422 in reference to FIG. 4, preferably one-way valve 22, placed just below outlet 4*b* of tube 4, prevents air from entering the reservoir if the reservoir empties and is exposed to the suction generated by arterial pump 1104. Though blood loss in liquid form is prevented from exiting outlet 4*b* of tube 4, blood in the form of foam may still do so. To limit blood foam from exiting the top of tube 4, a defoamer means is used to collapse the blood foam into liquid that then flows back down into blood chamber 2. This is illustrated in FIG. 2*a* by defoamer sponge 24, preferably incorporating anti-foam A and placed below valve 22, used to break up blood in the form of foam that reaches the inlet of valve 22. Placement of defoamer 24 at the top of tube 4 provides the desirable defoaming action while limiting contact between the defoamer and the blood.

As shown in FIG. 2*a* the large diameter of chamber 2 allows more time for the bubbles to rise to the top and causes less turbulence that could hinder the upward motion of the bubbles. Most of the blood preferably flows from chamber 2 to chamber 7 across screen 3, thereby assuring the upward motion of the bubbles. This preference is enhanced by cylinder 6 maintaining screen 3 free of contact with venous reservoir walls 18 and 19, see FIG. 2*c*. Typically, if wall screen 3 forms a cylinder with a 1" diameter, then for an 8" high structure, its surface area is 25 in². This large effective area is available for blood flowing from inlet chamber 2 to expandable chamber 8 and is virtually independent of the blood volume in expandable chamber 8. Annular space 7 formed by cylinder 6 and screen 3 and better seen in FIG. 2*c*, serves to separate gas from the blood; bubbles that cross wall 3 can still be buoyed upward to the top of chamber 7 where they can be removed by tube 9. The blood then flows from expandable chamber 8 to outlet port 5. Should air enter chamber 8, it can still float to the top of said chamber and be eliminated via tube 9. FIG. 2 *cc*, which is an enlargement of the circled section shown in FIG. 2*c*, illustrates how tube 9 forms air channels 9*aa*, described in reference to FIGS. 1*b* and 1*bb*, thereby enhancing air removal by keeping walls 18 and 19 slightly apart along the length of tube 9. Thus with this design, there are three chambers for air elimination: chambers 2, 7, and 8.

A major reason a collapsible bag is used as a venous reservoir is to prevent air from being pumped out of the bag and into the patient should the venous reservoir empty. In present bags this is achieved by having the outlet port (5 in FIG. 2*a*) at the lowermost point of the bag. This can be incorporated into the present invention. Alternatively, the inlet of outlet tube 5, 5*a*, can be cut on a diagonal (nominal 35° to 65°) with its pointed end protruding into expandable chamber 8 and its low point in line with the periphery of the bag at 8*c*, as shown in FIG. 2*a*. Tube 5 should be made of relatively soft material (e.g. 55 Shore A) and have a relatively large ID/wall ratio (e.g. 0.5"/0.062"=8). Since a larger ID/wall ratio, as well as softer durometer wall, requires a lower pressure difference across the wall of the tube to collapse the tube, then the combination of higher ratio and lower durometer can be used to quantify the ease of said collapse, (ID/wall)/durometer. Thus, for the above example, (0.5"/0.062")/(55)=0.147. This number is significantly higher than that obtained for the outlet tube typically used at the outlet of present venous reservoirs (0.5"/0.093")/(65) =0.082. Since the ease of tube collapse is related to $(ID/wall)^3$, (see my U.S. Pat. No. 5,215,450: Innovative Pumping System for Peristaltic Pumps), even a small change in that ratio causes a large change in ease of collapse. Thus, the softer tubing and/or high ID/wall ratio allows collapsing walls 18 and 19 of venous reservoir bag 1819 to gradually, rather than suddenly, impede the flow out of outlet tube 5. Once empty of liquids, the present aspect of the invention provides a looser seal about the outlet as compared to standard bags. Thus, when inlet flow resumes, less volume is needed to open the outlet tube, thereby providing resumption of flow sooner than present venous reservoir bags.

An experiment was conducted to determine the negative pressure developed between the outlet of venous reservoir 1103 and the inlet of pump 1104 when pump 1104 (see FIG. 1) was pumping at 6.0 L/min out of venous reservoir 1103 and the venous flow into the venous reservoir was less than 6.0 L/min. The reservoir was emptied and its outlet collapsed. Also measured was the blood volume required in the venous reservoir to reopen the venous reservoir outlet. Once emptied, the outlet of the Cobe reservoir bag stayed closed until the volume in the bag increased to over 1,400 ml. During that time, the pump inlet pressure (measured in line 135 in FIG. 1) decreased to and remained at over −600 mmHg. Once the blood volume in the bag reached 1,400 ml, sufficient pressure was exerted to expand walls and release the collapsed outlet of the venous reservoir, thereby allowing resumption of blood flow from the venous reservoir to the pump inlet. A similar experiment with the Baxter bag required an increase in blood volume of 400 ml before the high negative pressure at the pump inlet (−580 mmHg) was relieved and the bag outlet opened up. With the present invention, only 350 ml were required to open the venous reservoir outlet and reestablish flow, and the maximum negative pressure was only −400 mmHg.

As shown in FIGS. 2*a*, 2*b*, 2*c*, 2*d*, layers 18 and 19 are heat sealed (e.g., by radio frequency welding) by a double margin along their upper and lower edges, by a relatively wide seal along their right edge and by a narrower seal along their left edge. Anchoring holes (eyelets) 27, used to hang bag 1819, can be formed by punching holes through, and along, the top and bottom of the heat sealed surface. The preferred configuration includes a hole on both sides of inlet tube 1, outlet tube 5, and air-venting tube 4, and in the upper corner of the bag opposite tube 4 to facilitate secure attachment of the bag to the frame, see FIG. 2*a*.

It should be understood that various sizes of the venous reservoir can be made without necessarily affecting their performance; for example, three popular sizes having capacities of 400, 1200, and 2000 ml are some of the possibilities. To simplify manufacturing and reduce costs of the hardware, all reservoir sizes can have the same footprint so each size can utilize the same frame. Here, smaller capacity reservoirs have a smaller bag portion and larger peripheral area (FIG. 3). Anchoring holes 21*a*, 21*b*, 21*c*, 21*d*, 21*e*, 21*f*, and 21*g* used to attach each bag to the frame can be accommodated by corresponding adjustable supporting pins in the frame, for example, as well known in the art.

FIGS. 7*a*, 7*b*, and 7*c* illustrate another preferred embodiment of the present invention. Here, rigid cylinder 72 replaces perforated cylinder 6, shown in FIG. 2*a*, to provide annular space 77 as well as to serve as part of the wall of venous reservoir 772. Pliable venous reservoir walls 18 and 19 are sealed to rigid cylinder 72 on both sides of longitudinal slot 72*a*, said slot better seen in FIG. 7*b* (a cross sectional view of cylinder 72 along lines 25 and 25' in FIG. 7*a*) and 7*c* (a cross sectional view of cylinder 72 along lines 272 and 272' in FIG. 7*a*), providing fluid communication between annular space 77 and expandable outlet chamber 8. To reduce stasis and provide smooth blood flow, the incline at the bottom of the rigid cylinder 72, 72*d*, matches the bottom incline of chamber 8, 8*d*. Cylinder 72 (FIG. 7*b*) preferentially has longitudinal lips 72*b* and 72*c* along both sides of slot 72*a*, said lips tapering and thinning as they extend outward. These lips serve to seal venous reservoir walls 18 and 19 about slot 72*a* (e.g., by radio frequency welding) as well as to form a smooth blood flow path from annular space 77 to expandable chamber 8. It should be obvious that cylinder 72 preferentially is made of biocompatible, clear, rigid thermoplastic that can be easily sealed to venous reservoir walls 18 and 19. A good choice would be rigid PVC. It should be obvious that screen 3, air-venting tube 4, outlet tube 5, and expandable chamber 8 formed by walls 18 and 19 serve the same purpose described for the venous reservoir embodiment shown in FIG. 2*a*.

FIG. 7*d*, which is an enlargement of the circled section shown in FIG. 7*a*, illustrates another preferred embodiment providing a fluid path between chamber 8 and air-venting tube 74 that allows air removal present in annular space 77 and expandable chamber 8. Here, cylindrical air-venting tube 74 has a notch 74*h*, at its bottom, also seen in FIG. 7*e*, which is a view of FIG. 7*d* taken along cross section 26–26' and FIG. 7*f*, which is a view of FIG. 7*e* taken along cross section 27–27'. As shown, the height of notch 74*h* extends beyond top 26*b* of screen cage 26. Screen cage 26, as shown in FIG. 2*f*, has a top 26*b*, a bottom 26*a* and ribs 26*c*. Ribs 26*c* are also shown in FIG. 2*c* (a cross sectional view along 16–16' of FIG. 2*a*) as well as in FIGS. 7*a*, 7*b*, and 7*d*. The bottom of notch 74*h* extends onto the highest point of chamber 8, 8*a*, which also preferentially corresponds to the highest point of screen 3. Thus, notch 74*h* provides a fluid communication, see arrow 84 in FIG. 7*d*, between air-venting tube 74 and chamber 8. Notch 74*h* replaces the function of tube 9 shown in FIG. 2*a*.

As described so far, air removal is accomplished as it is by current techniques: suction pump 1114 (see FIG. 1) typically with ¼" ID tubing is used to remove the gas from the top of the venous reservoir. This arrangement works but requires constant vigilance and intervention by the user to control air removal. Another innovative feature of the present invention is that air can be automatically eliminated from the reservoir with little or no user intervention required. Three preferable designs for the air purge port use a hydrophobic membrane, a floating ball, or controlled suction. All three methods allow air to be removed with very little, or no blood loss. The user would have the option to connect wall suction or one of the sucker pumps as the suction source for the air purge port, preferably having some regulating means to adjust/limit the degree of suction.

FIG. 4 illustrates one preferred embodiment that achieves a large membrane area at the top of the venous reservoir. The design, with a cross section in the shape of an inverted "V" or "U", achieves a large area and provides an inclined surface. Membrane 45 has an inclined surface that facilitates clearing of any blood film off the surface of the membrane. Gravity and wicking should encourage any such film to "peel" off the surface into the blood pool, thereby maintaining the membrane clearer and the gas transfer rate up. Membrane support 425 can be incorporated as the top of a semi-rigid PVC frame formed into a protective "roof". The inside surface of the roof-contacting membrane incorporates ridges 425a, which are in unimpeded fluid communication with air-venting tube 44. Ridges 425a also support membrane 45 and prevent it from deforming due to pressure differences across its wall. The membrane should meet a high gas flow elimination requirement (at least 1 L/min at −100 mmHg). Membranes preferably are made of PTFE (e.g. Durapel™ from Millipore, Bedford, Mass.) or polypropylene (e.g. Zintex™ from W L Gore, Elkton, Md.), preferably having a pore size between 0.45μ and 1.0μ. The small pore provides a sterile barrier.

The membrane is used to automatically remove air 423 that may accumulate at the top of the venous reservoir by applying suction (from the hospital supply) to air-venting tube 44. Hydrophobic microporous membrane 45 prevents the loss of blood 46 from the venous reservoir. Thus the combination of the hydrophobic membrane and suction applied to the external side of the membrane provides means to automatically remove the air from the blood chamber without blood loss.

Another preferred embodiment, shown in FIGS. 5a and 5b, utilizes a tubular microporous membrane 55 in fluid communication with purge port 54, said tubular membrane internally supported and sealed to perforated rigid housing 525. Perforated rigid housing 525 allows gas to cross membrane 55 and enter chamber 59 unimpeded. Housing 525 is sealed at the bottom along 525a. Chamber 59, formed by housing 525, is in fluid communication with purge port 54. Annular space 57 is formed by circular membrane 55 and air-venting tube 4. Air-venting tube 4 could be in fluid communication with first inlet chamber 2 shown in FIG. 2a and preferably located on top of chamber 2. Normally annular space 57 is filled with blood. Should air 523 enter line 1 (see FIG. 2a), it would rise up chamber 2, as shown in FIG. 2f, enter annular space 57 (FIGS. 5a and 5b), across membrane 55 into chamber 59 (FIG. 5a), across port 522a of one-way valve 522, and be purged via purge port 54. Applying suction to purge port 54 facilitates air removal by increasing the pressure difference across membrane 55. As with the "roof" design referenced in FIG. 4, vertical placement of the tubular membrane 55 facilitates "peeling" of the blood layer off of the surface of the membrane, thereby improving long-term gas transfer.

Figure 6A:
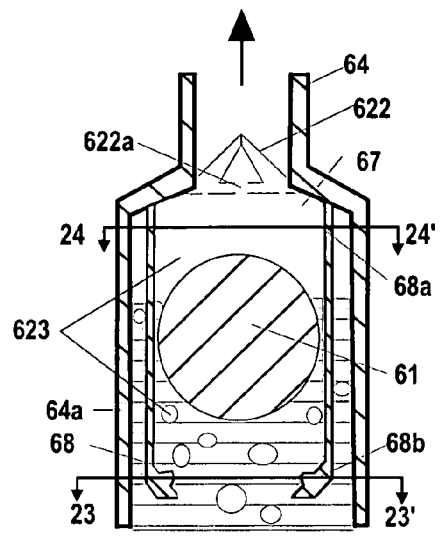
FIG. 6a is a line drawing illustrating one preferred embodiment of the present invention where air removal is automated by utilizing a floating ball valve.

The second preferred method to automatically remove air utilizes a floating ball, which allows air but not blood to be removed through the purge port. As shown in FIG. 6a, housing 64a forms chamber 67 that allows air bubbles to rise unhindered as previously described for chamber 2 and tube 4 in reference to FIG. 2a. Housing 64a incorporates ball cage 68, floating ball 61 and unidirectional valve 622. Port 622a of unidirectional valve 622 providing fluid communication between chamber 67 and gas exhaust port 64, is open as long as air 623 is present in chamber 67. When most of the air has been eliminated, the rising fluid level brings ball 61 to the top of chamber 67, effectively closing port 622a. In this position, any further withdrawal of fluid from the venous reservoir is prevented. When more air enters the reservoir, the blood level falls, ball 61 drops, and the applied suction removes air 623. Suction may be provided by a wall source or a suction pump, but preferably is controlled for the purpose described below.

Figure 6B:
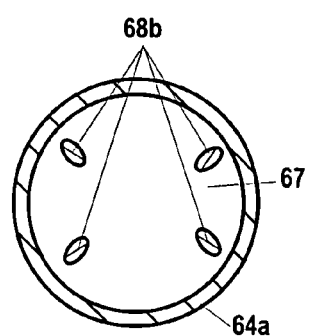
FIG. 6b is a line drawing illustrating another view of the bottom of the ball cage used in FIG. 6a taken along line 23–23'.
Figure 6C:
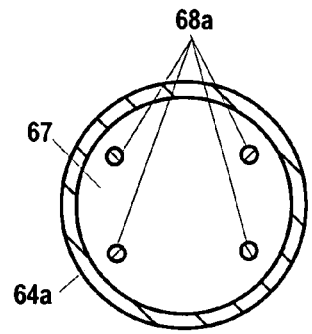
FIG. 6c is a line drawing illustrating another view of the ball cage used in FIG. 6a taken along line 24–24'.
Figure 6D:
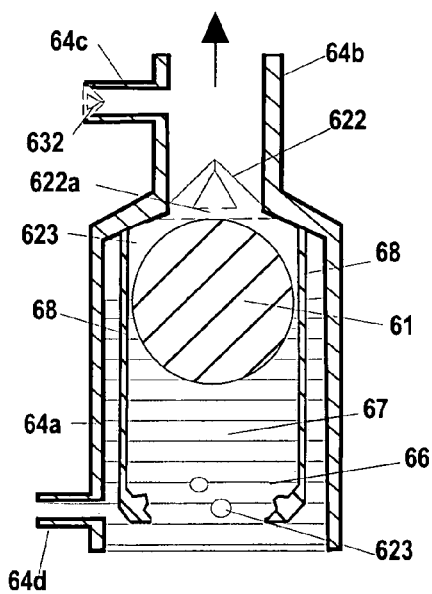
FIG. 6d is a line drawing illustrating another embodiment of the present invention where air removal is automated by utilizing a floating ball valve incorporating two safety features.

There are two forces maintaining ball 61 up against port 622a keeping said port closed: the buoyancy of the ball and the suction force applied at the gas port (Fs). $Fs=(\pi d2S/4$, where d is the inside diameter of air port 622a in contact with ball 61, and S is the negative pressure (suction) applied via air-venting tube 64 against said ball. The upward force, Fs, must be less than the weight of the ball so that when the blood level drops, the weight of the ball overcomes Fs and the ball falls. Cage 68, in general has a larger ID than the OD of ball 61, see 68a in FIGS. 6a and 6c, where FIG. 6c is a line drawing illustrating another view of the ball cage used in FIG. 6a taken along line 24–24'. Cage 68 aligns the ball with air port 622a. The bottom of cage 68 narrows down to an ID smaller than the OD of ball 61, see 68b FIGS. 6a and 6b, where FIG. 6b is a line drawing illustrating another view of the bottom of the ball cage used in FIG. 6a taken along line 23–23'. The smaller ID 68b serves to retain ball 61 within its chamber 67 and prevents it from falling into the venous reservoir. For this design, for example, ball 61 may be a 1" solid polypropylene ball (specific gravity sp=0.90), or a hollow ball (where sp is adjustable). Air port seal 622a could, for example, be made of soft silicone and the ID of the air port may be ¹⁄₃₂". To assure a good seal, the surface of the ball should have a fine finish, preferably with a tolerance of 0.001" or better. The applied suction should be low to assure that ball 61 does not "stick" to gas port 622a in the closed position, and to minimize blood damage. For example, a pressure of −30 mmHg can be applied to remove the air. This degree of suction is sufficient to withdraw the air and maintain the liquid column within first and second inlet chambers 2 and 7 when flexible chamber 8 is less than full, see FIG. 2a. As shown, the suction means to remove the air is a regulated vacuum source. The automatic means to remove air with little or no blood loss is the ball opening to allow suction to remove air, and closing to prevent blood loss. This combination of ball valve and regulated suction is similar in function to that shown in reference to FIG. 2a wherein the level sensor (here the floating ball) is the means to sense the presence of air and automatically control suction application. In one of the embodiments of FIG. 2a, it is the tubing clamp opening the tube (and here the ball dropping) to apply vacuum to remove air and clamping off the tube (here the ball rising against the valve seat) to stop suction to prevent blood loss. To prevent excess suction (e.g. over −150 mmHg) from being applied, the line between air venting tube 64 and the suction source can include a t-connector 64c with a suction regulating valve 632 attached at the inlet of side port 64c (FIG. 6d). Such valves are commercially available at various cracking pressures and are currently used for IV infusion sets (e.g., NP Medical, Clinton, Mass., cost <$0.25). As well known in the art, blood trap (not shown) may be incorporated so any blood that may enter the line would not progress to the suction source, and, in fact, blood loss may be returned to the patient. This can also be achieved by connecting air-venting tube 64 at 64b to Cardiotomy reservoir 1115 (see FIG. 1), to which suction is applied.

Figure 11:
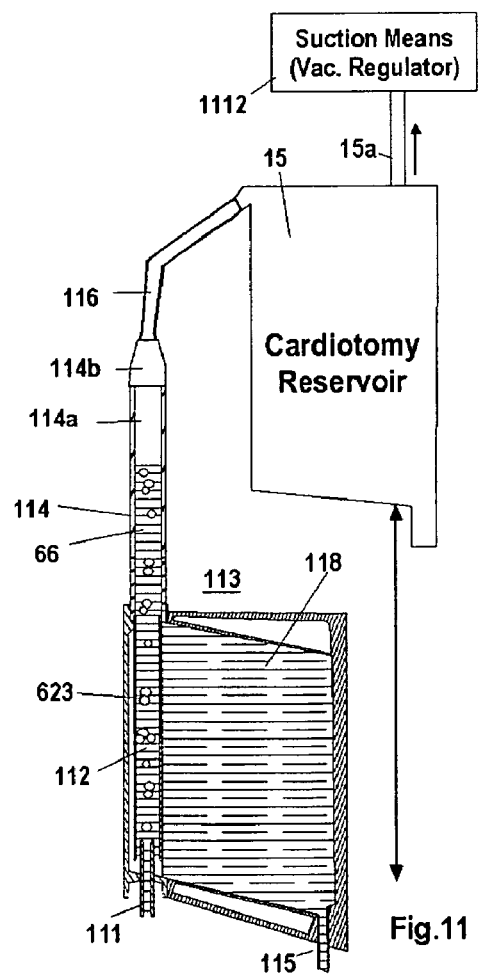
FIG. 11 is a line drawing illustrating another embodiment of the present invention where air removal is automated by connecting the gas exhaust port of the venous reservoir to the inlet port of a cardiotomy reservoir, said cardiotomy having a regulated negative pressure applied to it.

Another preferred method to remove air is a variation of the second method but without the floating ball valve combination. As shown in FIG. 11, the top of first inlet chamber 112 of venous reservoir 113 is extended into "chimney" 114 that serves to vent air and is connected to cardiotomy reservoir 15, to which suction is applied at 15a. The degree of suction should be sufficient to elevate the blood level into chimney 114, even when the expandable chamber 118 is less than full. Thus, any air 623 entering inlet tube 111 would float to the top of first inlet chamber 112 and enter chimney 114. The air would then displace the liquid in chimney 114, coalesce with air volume 114a that interfaces between the blood in chimney 114 and outlet 114b of chimney 114, and the additional suction would pull the liquid up the chimney to its original level. This system requires that chimney 114 have an ID that facilitates upward movement of air bubbles, even large ones. The length of the chimney needs to be at least equal to the level of the expected level of liquid column 66 when suction is applied to chimney 114 and expandable chamber 118 is full. Beyond that height, the outlet of chimney 114b can be connected via ¼" ID tube 116 to cardiotomy reservoir 15. Air space 114a maintained below chimney outlet 114b assures that the blood does not enter smaller diameter tube 116. Suction, applied at 15a, can be provided by the wall source, or suction pump 1114 (FIG. 1) connected to cardiotomy reservoir 15, said suction regulated (e.g. by a vacuum regulator) to appropriate levels as well known in the art. It should be obvious that the suction applied to tube 116 equals that applied to the cardiotomy reservoir. Further, when regulated wall suction is used then the means to control the suction to automatically remove the air is vacuum regulator 1112.

As described in the Description of the Prior Art, improved venous drainage can be achieved by applying some negative pressure on the venous blood. Another aspect of the invention allows the user to apply suction with a collapsible reservoir. FIGS. 8a, 8b, and 8c illustrate venous reservoir 772, previously described in reference to FIGS. 7a, 7b, and 7c, placed in generally elliptical, clear rigid, housing 88. Housing 88 is open both at its bottom, defined by border 88a, and at its top, defined by border 88b, said borders having sealing gaskets 82 and 81 respectively. FIGS. 8a, 8b, and 8c illustrate venous reservoir 772, previously described in reference to FIGS. 7a, 7b, and 7c, placed in generally elliptical, clear rigid, housing 88. Bottom cap 89 also is sealed to inlet tube 1 at 89a and outlet tube 5 at 89b. A similar arrangement is made at the top of venous reservoir 772 where rigid disk 72d is sealed along top gasket 81 of housing 88. Thus, the user would slip chimney 74 of disposable venous reservoir 772 into the bottom of housing 88, push it up and insert it through opening 88d at the top of housing 88. When lined up, rigid disk 72d is pushed against gasket 81 and bottom cap 89 seals against gasket 82. The bottom and top seals are reinforced and maintained by cap 89 held against housing 88 by snaps 88e, 88f, 88g and 88h that lock onto ridge 89d of cap 89. At the end of the case, snaps 88e and, 88f shown in FIG. 8b, and snaps 88g and 88h shown in FIG. 8a, each of which is hinged at its midpoint (e.g. see 88i of hinge 88f) are pushed inward, as shown by respective arrows 812 and 811 for snaps 88f and 88e, causing the bottom of said snaps (e.g. 88j shown in FIG. 8b) to move outward, see for example 88e' in FIG. 8b, releasing said snaps from locking ridge 89d and 89j thereby allowing the removal of venous reservoir 772.

Chamber 87, formed between venous reservoir 772 and rigid housing 88, communicates via port 88c with vacuum regulator 813, said regulator used to adjust the degree of suction applied to chamber 87 using knob 813b. Gauge 813a can be used to indicate the applied suction. As described before, venous reservoir 772 responds to pressure differences across its walls 18 and 19 (FIG. 8b). Thus, diminished blood flow from patient 1102, see FIG. 1, due to increased resistance to flow (e.g. smaller cannula) can be increased by applying suction to chamber 87. The suction "pulls" walls 18 and 19 outward thereby pulling the blood into the blood chamber. For safety, housing 88 is sized to assure that venous reservoir 772 cannot over-expand beyond defined limits, said limits defined as a volume in blood chamber 8 that would result in a pressure measured at the top of blood chamber 8 being greater than 10 mmHg. Thus, as chamber 8 of venous reservoir 772 expands, walls 18 and 19 move towards the walls of housing 88 until they make contact, see 18a and 19a in FIG. 8b. Once contact is made, further outward motion of walls 18 and 19 is limited by rigid housing 88. To facilitate the use of the system, housing 88 incorporates pole clamp 810, said clamp provides a simple connection of said housing to a heart-lung machine. It should be understood that a rigid component, such as rigid cylinder 72, incorporating into venous reservoir 772, see FIGS. 7a and 8a, is required to facilitate both the introduction of said venous reservoir 772 into housing 88, and the sealing of said reservoir against gasket 81, shown in FIG. 8a. To enhance the ability of the user to see the blood in venous reservoir 772, light 80, shown in FIG. 8b, can be added to the back of housing 88.

Figure 9A:
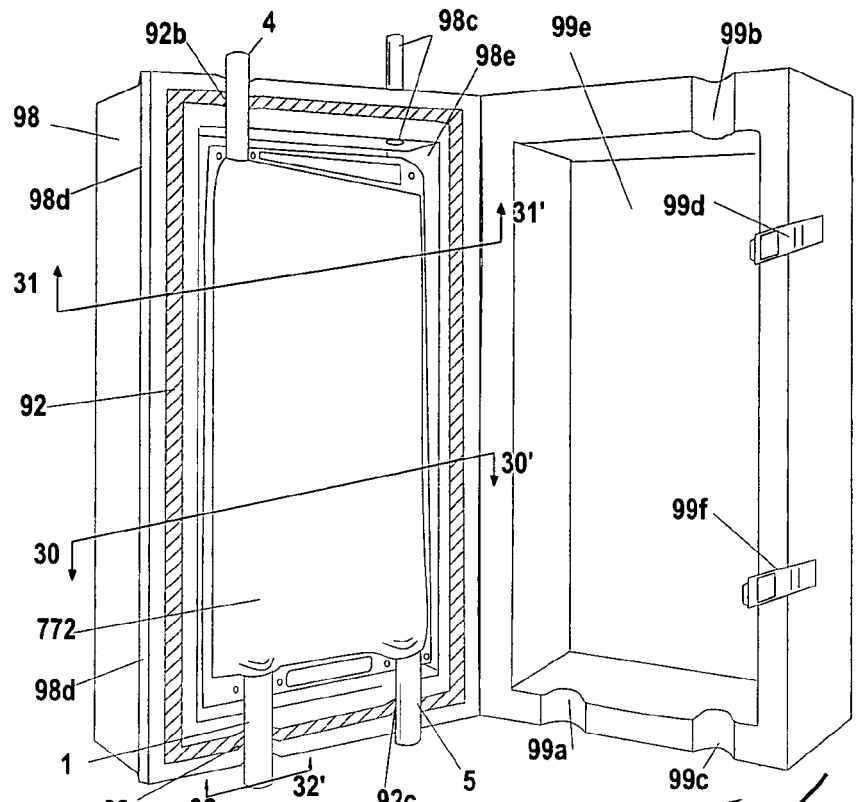
FIG. 9a is a line drawing of another preferred embodiment of the present invention wherein the venous reservoir can be sealed within a rigid housing where suction can be applied to the external flexible walls of said reservoir thereby providing venous augmentation.
Figure 9E:
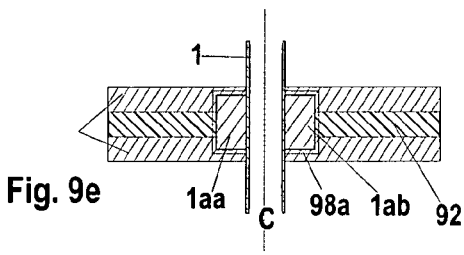
Figure 9F:
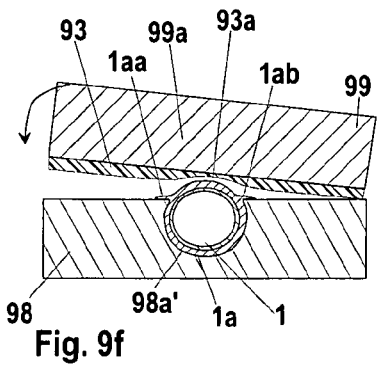
FIG. 9f is a line drawing identical to that shown in FIG. 9d except that this embodiment incorporates a gasket having an indentation to seal about the inlet tube of the reservoir, and a deeper indentation in the housing to support said tube while the venous reservoir is loaded.
Figure 9C:
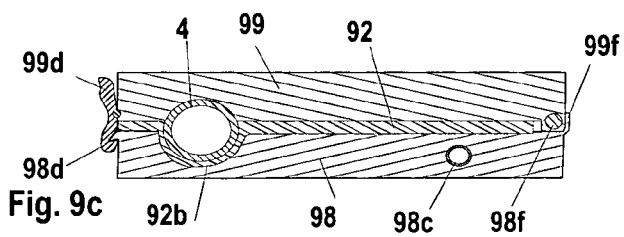

FIG. 9a illustrates another embodiment for a nondisposable housing designed to allow venous augmentation with a collapsible venous reservoir. The concept is similar to that shown in FIG. 8a except that the seals and closure mechanism are different. Here, venous reservoir 772 is placed in container 98, said container having a back plate and four walls forming first open box, 98e, which accommodates venous reservoir 772. Container 98 has a matching door 99 that is hinged at 99f by pin 98d to container 98 and is shown in FIGS. 9b and 9c. Door 99 has a front plate and four walls forming second box 99e that also accommodates venous reservoir 772. To operate, venous reservoir 772 is placed in first box 98e and door 99 is closed thereby sealing said venous reservoir, along gasket 92, within sealed space 909 formed by first box 98e and second box 99e. Port 98c in box 98 is in fluid communication with the formed sealed space, and preferably is connected to a regulated vacuum source, much like the one described in reference to port 88c shown in FIGS. 8a and 8b. It should be understood that for proper function, the venous reservoir is free to expand within the sealed space 909 thus formed. For free expansion of venous reservoir 772, seals of the venous reservoir within container 98 and door 99 are achieved at inlet tube 1, between 92a and 99a (FIG. 9b), air-venting tube 4, at 92b and 99b (FIG. 9c), and along outlet tube 5, at 92c and 99c (FIG. 9b). When door 99 is closed, the ID of indentations 92a and 99a form a tight seal about the OD of inlet tube 1. Similarly, indentations 92c and 99c form a tight seal about the outside of outlet tube 5 (FIG. 9b), and indentations 92b and 99b form a tight seal about the outside of air-venting tube 4 (FIG. 9*c*). To assure a tight seal, relievable latches 99*d* lock unto ridge 98*d*, see FIGS. 9*a*, 9*b* and 9*c*.

Figure 9D:
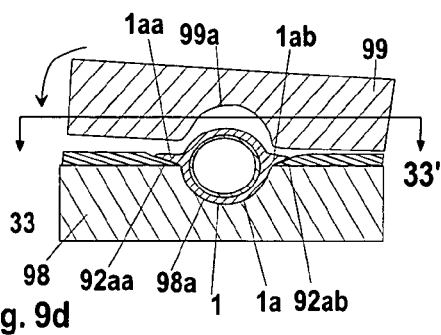
Figure 9B:
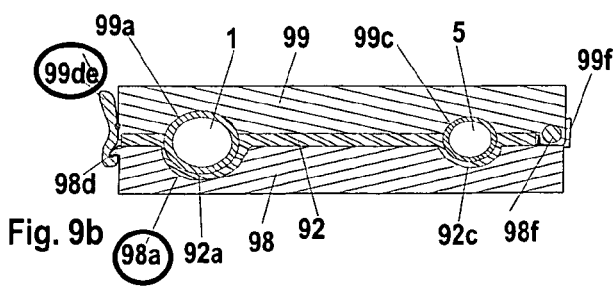

To improve the seal along the inlet, outlet and gas exhaust port, each of said tubes preferably incorporates a secondary structure, see sealing structure 1*a* in FIG. 9*d* for inlet tube 1. Sealing structure 1*a* has a flexible wall forming wings 1*aa* and 1*ab* on the side of tube 1, see FIGS. 9*e* and 9*d*. The wings are tapered, being thickest at the base and thinnest at the tips, see FIG. 9*d*. For effective sealing, gasket 92 accommodates wing 1*aa* at thinner section 92*aa* and wing 1*ab* at thinner section 92*ab*, said accommodation providing a seal between container 98 and door 99 along gasket 92. Gasket 92, for example, can be made of a polyurethane sponge, which conform to the shape of said wings, see FIG. 9*d*. Wing 1*a* preferably is bonded or welded to tube 1 and is therefore disposed when venous reservoir 772 is disposed. In one preferred embodiment, shown in FIGS. 9*b*, 9*c* and 9*d*, indentation 98*a* in the housing 98 and indentation 99*a* in door 99 approximate half the outside diameter of inlet tube 1. Similar designs can be incorporated to seal venting tube 4 and outlet tube 5.

FIG. 9*f* illustrates another preferred embodiment for sealing inlet tube 1 between housing 98 and door 99. Here, gasket 93 is attached to door 99, said gasket having indentation 93*a* to seal about the inlet tube 1 when door 99 is closed against housing 98. This design also incorporates deeper indentation 98*a*' in the housing, with a closed circumference greater than 225° and an inside diameter that is less than the OD of inlet tube 1. When the venous reservoir is loaded into the housing, flexible inlet tube 1 is pushed into indention 98*a*' where it is retained within said indentation by a pressure fit. This allows the user to load air-venting tube 4 and outlet tube 5. It should be obvious that purge port should be loaded first thereby having the venous reservoir hanging from the top while the other two tubes are lined up before door 99 is closed.

Figure 12A:
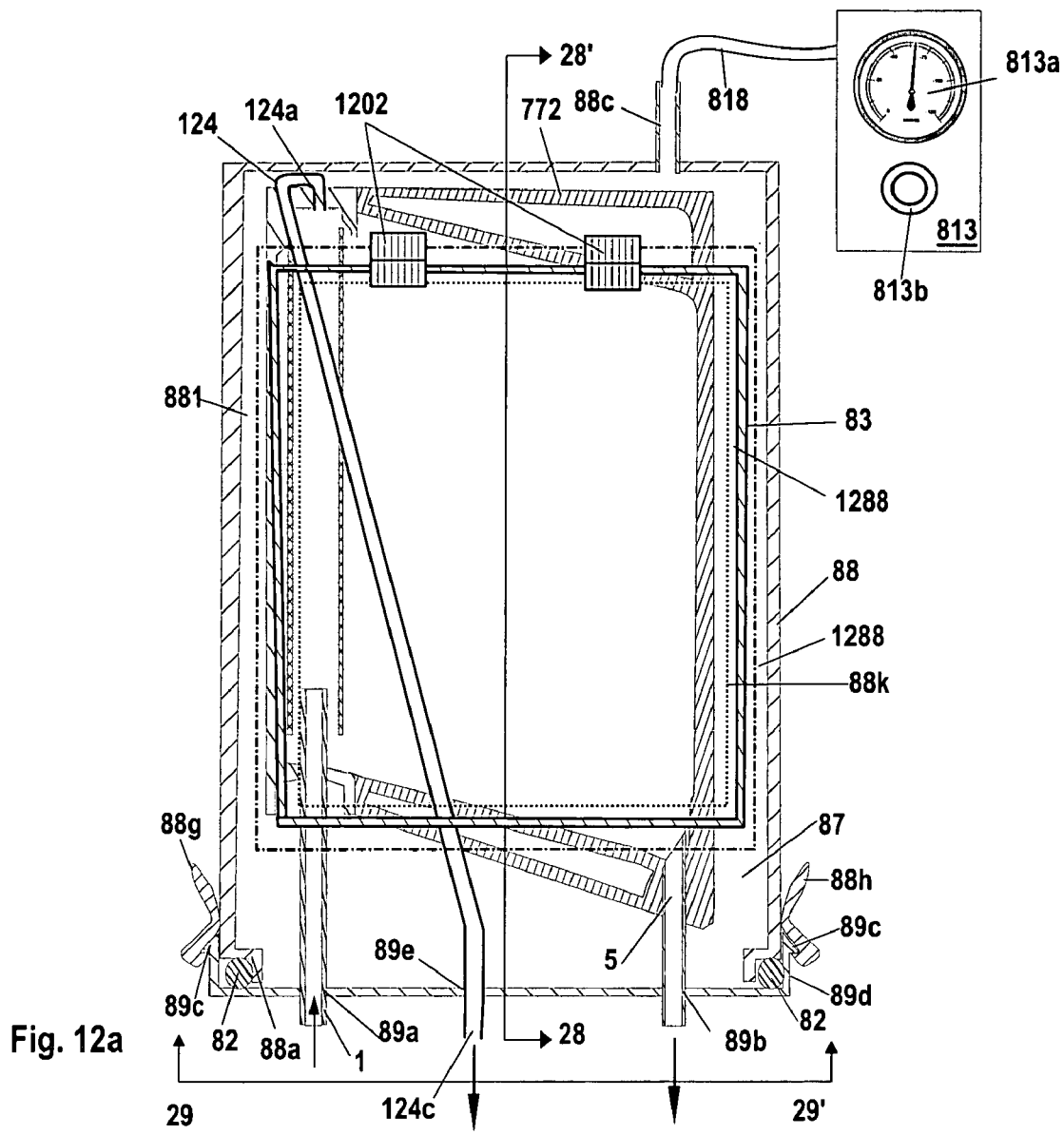
FIG. 12a is a line drawing illustrating another preferred embodiment of the present invention, similar to that shown in FIG. 8a, except that all the tubes entering the bag enter from the bottom and incorporate a disposable cover plate.
Figure 12C:
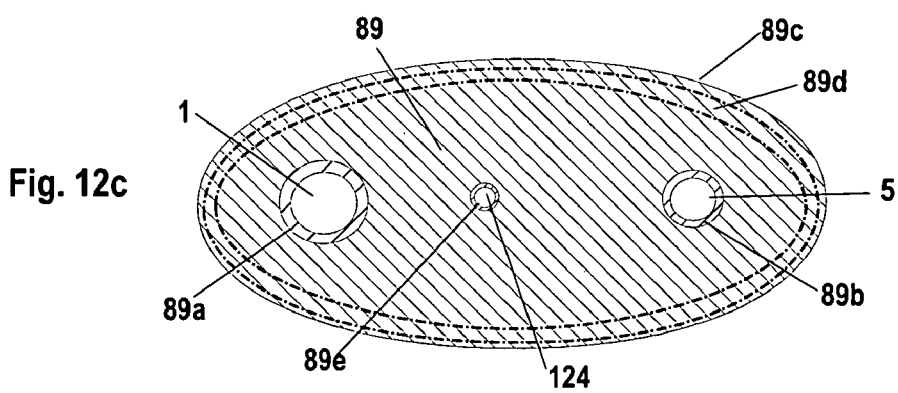
FIG. 12c is line drawing of a cross section taken of a bottom view of cover 89 of FIG. 12a along line 29–29'.
Figure 12B:
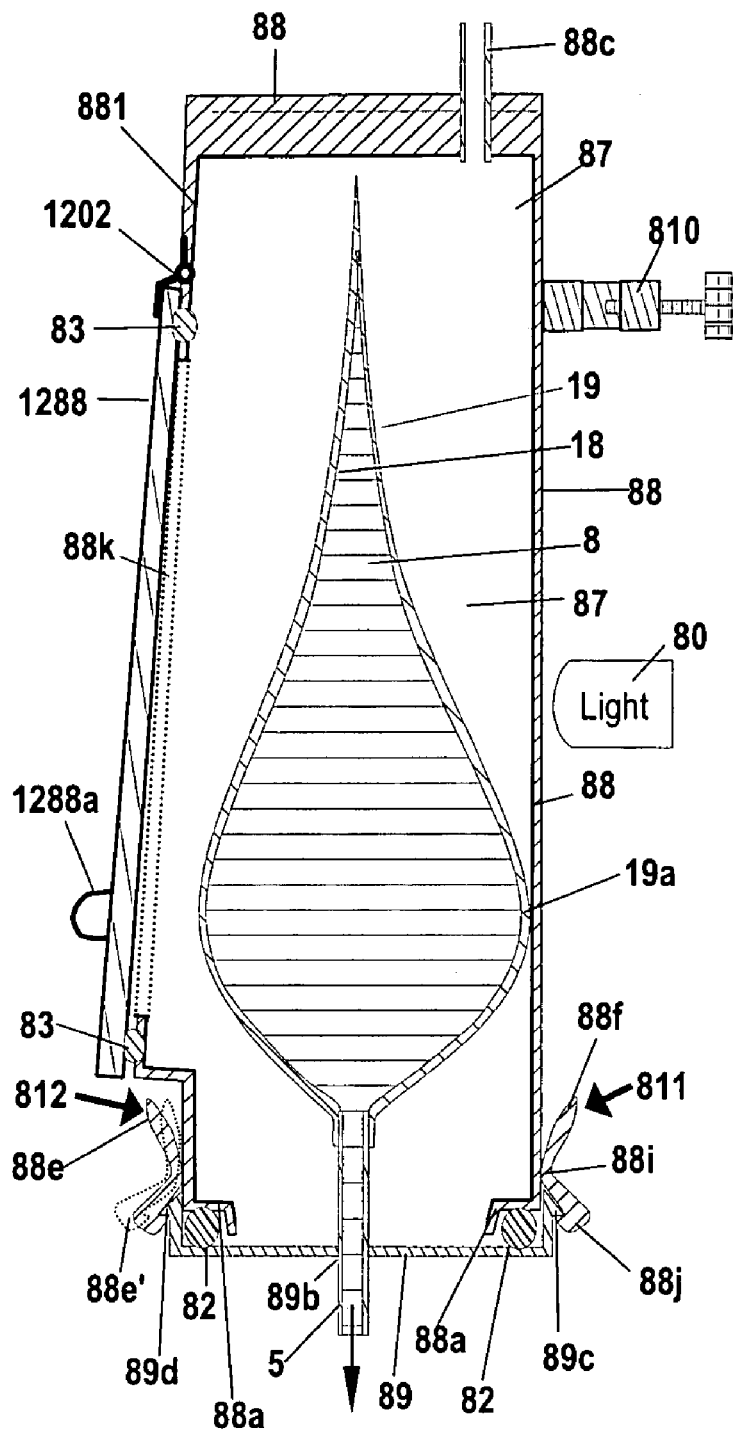
FIG. 12b is a line drawing of a cross section taken of FIG. 12a along line 112–112'.

FIGS. 12*a*, 12*b*, and 12*c* illustrate another preferred embodiment that is identical to that described in FIGS. 8*a*, 8*b* and 8*c* with two major exceptions. Gas removal port 74 and its associated seal 72*d* shown in FIG. 8*a* are replaced by gas removal tube 124 shown in FIG. 12*a*. Tube 124 bends and extends to the bottom of bag 772, see FIG. 12*a*, and exits in the same direction as inlet tube 1 and outlet tube 5 thereby eliminating the need for top seal 72*d*. Bag 772 in FIG. 8*a* has its gas removal port 74 extending straight up with its outlet ending above bag 772 and pointing opposite to said inlet and outlet tubing. Having all three tubes of bag 772 extend beyond blood chamber 8 and in one direction and exit along the same plane allows all three tubes to be threaded, preferably during manufacturing, through bottom supporting plate, or cover 89. Thus, as shown in FIGS. 12*a*, 12*b*, and 12*c*, inlet tube 1 is threaded through cover 89 and is sealed at 89*a*, outlet tube 5 is threaded through cover 89 and is sealed at 89*b*, and gas removal 124 is threaded through cover 89 and is sealed at 89*e*. Having all tubes extend beyond blood chamber sealed within single plate 89 significantly simplifies sealing bag 772 in housing 88; it allows sealing along a single plane of cover 89 against single O-ring 82 of housing 88. It should be obvious that bottom plate 89 could incorporate perfusion connectors as described in reference to supporting plate 1389 in FIG. 13*f*.

The other innovative design, shown in FIGS. 12*a* and 12*b* but not in FIG. 8*a* or 8*b*, incorporates an opening 88*k* in front wall 881 of housing 88 allowing the user to reach bag 772 without removing the bag from its housing. Reaching bag 772 was the purpose of the external means provided by aforementioned US Pat. '045 to massage the SSR with vibrator 36. The present invention incorporates removable sealing means to front wall 881 of housing 88, such as door 1288, whose outside outline is shown as a dashed line in FIGS. 12*a* and 12*b*. Door 1288 in its neutral state is supported by hinge 1202 hanging at on front wall 881. The outside perimeter of opening 88*k*, shown as a dotted line in FIGS. 12*a* and 12*b*, of front wall 881 is surrounded by flexible seal 83. Seal 83 assures that when door 1288 is closed, it seals opening 88*k* from atmospheric pressure. To open door 1288, the user would release any negative pressure in closed chamber 87 then open door 1288 by pulling handle 1288*a* shown in FIG. 12*b*. Closure of door 1288 against seal 83 can be facilitated by tilting front wall 881 either by design, or by tilting entire housing 88, thereby allowing gravity to hold door 1288 against wall 881. Design correctly, using gravity to push door 1288 against seal 83 can eliminate clamps that may be necessary otherwise. Gravity closing would allow hinged door 1288, if it were not secured to rigid housing 88, to also serve as a pressure relief valve should vacuum fail. As well known in the art of doors, mechanisms to maintain door 1288 open, or even temporarily remove the door, can be easily incorporated in the usual manner. To assure that vacuum is not applied accidentally, door closure is preferably designed such a complete seal occurs only when vacuum is applied and the user temporarily pushes against the door. The seal formed by the initial pushing force provided by the user, is then maintained once vacuum build within chamber 87.

FIGS. 13*a* and 13*b* illustrate another preferred embodiment of a soft shell reservoir with the very innovative features: top loading of the reservoir into its holder and easy secure sealing of the bag for vacuum assist. Venous bag 1366 is preferably made by RF welding polyvinylchloride or polyurethane film having thickness of 0.015 to 0.020" along perimeter 1310, to form expandable chamber 138 with walls 1318 and 1319. Folded screen 1303 (e.g. Medifab from Tetko Inc. Depew N.Y., a polyester mesh with a pore size of 105μ and a 52% opening) is placed with fold (preferably not creased) 1303*a* facing downward and sealed along its vertical sides by welding its side edges between walls 1318 and 1319 along periphery 1310. Screen fold 1303*a* defining the bottom of screen 1303, preferably is placed at least ½" from the bottom of blood chamber 138. The top free edges 1303*b* and 1303*c* of screen 1303, shown in FIG. 13*b*, face upward and, at least partially, are not sealed along the top periphery 1310*a* and therefore an opening into pouch formed by fold 1303*a* and the two sealed sides of screen 1303. The screen placement defines four sections, within expandable chamber 138. Bottom or outlet section 138*a* defined as the section of blood chamber between screen fold 1303*a* and blood outlet tube 1305. Mid or inlet section 138*b* defined as the section of blood chamber between the top of screen 1303 and its fold 1303*a*. In inlet section 138*b*, blood is completely surrounded by screen 1303. Top, or bubble removal section 138*c*, is defined as the section of blood chamber 138 above inlet section 138*b*, between the top of screen 1303 and sealed top periphery 1310*a*. Bubble removal section 138*c* has no screen. The "in-between" section, 138*d*, is the section between walls 1318 and 1319 and screen 1303. The four sections are in fluid communication with each other.

As shown, four tubes enter bag 1366. Inlet tube 1301 and infusion tube 1306 are in direct fluid communication with inlet section 138*b*. Air removal tube 1304 is in direct fluid communication with inlet section 138*b* and air removal section 138*c*. Outlet tube 1305 is in direct fluid communication with outlet section 138*a*. Tubes 1301, 1306 and 1304 enter from the top of blood chamber 138, are sealed along top perimeter of sealed section 1310*a*, pass through air removal section 138*c*, two screen edges 1303*b* and 1303*c* of screen 1303 and into inlet section 138*b*. All tubes, except outlet tube 1305, preferably have holes along their length positioned in inlet section 138*b*. Gas removal tube 1304 also has holes, 1304*aa*, along its length stationed in both air removal section 138*c* and inlet section 138*b*.

Inlet tube 1301 preferably enters blood chamber 138 at a top corner of blood chamber 138 and extends to the bottom of inlet section 138*b*, preferably diagonally to a bottom corner opposite said top corner. Blood enters inlet tube 1301 at its inlet end 1301*a* in a downward direction, said inlet being above said blood chamber 138 and changes direction as it flows within curved inlet tube 1301. Outlet end 1301*d* of inlet tube 1301 is preferably sealed, forcing blood out exiting holes 1301*b*. Exit holes 1301*b* are preferably located only along the top length of tube 1301 situated in inlet section 138*b* that faces air removal section 138*c*, see FIG. 13*a*. Thus, venous blood, entering inlet tube 1301 in a downward flow at inlet 1301*a*, is diverted from a downward flow to a more horizontal flow and then in an upward direction through exit holes 1301*b*. The diversion in flow occurs within inlet tube 1301 distal to inlet 1301*a*. The upward blood flow pushes bubbles towards air removal section 138*c*. A venous bag for an adult patient would preferably have inlet tube 1301, said tube preferably having an ID of 0.5" and exit holes 1301*b* with a diameter of 0.5" or larger.

Blood entering inlet section 138*b* preferentially flows to outlet section 138*a* via screen 1303, said screen, once wet, allowing liquid through but retaining bubbles within inlet section 138*b*. Bubbles are pushed upwards by the direction of the blood exiting holes 1301*b* and by buoyancy. Bubbles rise towards air removal section 138*c* and then to access holes 1304*a* of air removal tube 1304, where they are removed, is obstructed when wall 1318 collapses against its opposing wall, as happens with prior art SSR when blood volume is low. With the present SSR, as described in reference to FIG. 2 cc and FIGS. 1*b* and 1*bb*, channels are formed along the outside diameter of tubes 1301, 1306, and 1304 providing a pathway for bubbles to move upward to air removal section 138*c* and on to access holes 1304*a* of air removal tube 1304. Air removal efficiency is further improved by extending tube 1304, and preferably also infusion tube 1306, from the top of blood chamber 138 downward into inlet section 138*b*, at least 50% of the vertical distance between the top and the bottom of inlet section 138*b* but preferably over 80% of the height inlet chamber 138*b*. If no screen is used, then said extension downward from the top of blood chamber 138 is at least 50% of the height of blood chamber 138.

As shown in FIG. 13*a*, air removal tube 1304 preferably extends in a diagonal direction within blood chamber 138*b* thereby providing a longer air removal channel than that possible with said tube extending only vertically. Tube 1306 serving as an infusion line, may be closed at its top and just serve as a spacer that provides air bubbles a pathway to air removal section 138*c* when low blood volume tends to collapse the blood chamber. In fact additional intermediate gas purge tubes (not shown), similar to tubes 1304 and 1306 may be incorporated in a similar manner to provide more numerous air removal channels. Having air channels from the bottom of the screen to the air removal section, not only eliminates the front plate of prior art venous reservoir, but also allows chamber 138 of bag 1366 to take its natural tear drop shape, much like that shown in FIG. 12*b*. The teardrop shape provides a larger area of the screen (the bottom) for blood flow unhindered by contact with the walls of the bag.

To assure that air bubbles can travel along the entire horizontal length of air removal section 138*c* towards air removal tube 1304, spacer 138 cc may be placed along the top of blood chamber 138. Spacer 138 cc prevents the flexible wall forming blood chamber 138 from completely collapsing against its opposing wall when the blood chamber is partially empty. As with the aforementioned air channels provided by tube 1304, preventing said complete collapse increases the efficiency of gas from the top of blood chamber 138.

Another innovative design feature requires that the open ends of the all tubes of venous reservoir 1366 be above blood chamber 138. Inlet tube 1301, gas removal tube 1304 and infusion tube 1306 enter blood chamber 138 from its top. Outlet tube 1305 exits outlet blood chamber 138*a* in a direction that facilitates outlet flow to exit in an upward direction. For example, as shown in FIG. 13*a*, tube 1305 exits outlet pocket 138*aa*, the lowest portion of outlet 138*a*, in a horizontal direction thereby requiring only 90° turn for changing the normally downward outlet flow to the desirable upward flow. Here the venous reservoir also incorporates supporting plate 1389 having a first and second planar surfaces, with said first planar surface facing blood chamber 138. The tubes of venous reservoir: inlet tube 1301 at 1389*a*, outlet tube 1305 at 1389*b*, gas removal tube 1304 at 1389*c*, and infusion tube 1306 at 1389*d* can be threaded through, solvent bonded and sealed during manufacturing to supporting plate 1389: (inlet tube 1301 at 1389*a*, outlet tube 1305 at 1389*b*, gas removal tube 1304 at 1389*c*, and infusion tube 1306 at 1389*d*.) Supporting plate 1389 can serve to support bag 1366 by dropping it into holder 1388, as is done with prior art hard shell reservoir (e.g. Baxter holder p/n HSRH for hard shell reservoir p/n HSR4000). For this purpose, the perimeter of supporting plate 1389 is preferably larger than the perimeter of venous reservoir 1366.

Inlet 1305*a* of outlet tube 1305 tube may also be designed to prevent pocket 138*aa*, shown in FIG. 13*a*, from prematurely collapsing (i.e. while there is still blood in outlet chamber 138*a*) and uncollapsing once blood returns to outlet chamber 138*a*. This is achieved by having the inlet of tube 1305 cut longitudinal to form a scoop-shape whose walls provide the resilience to maintain the walls of bag 1366 of section 138*aa* apart from each other. A similar design was described in reference the inlet 5*a* of outlet tube 5 shown in FIG. 2*a*.

Another advantage of having all the tubes for the SSR entering from its top is that the bottom of the bag is unhindered by tubing and can be placed lower on to the floor thereby allowing greater gravity drainage.

Figure 13D:
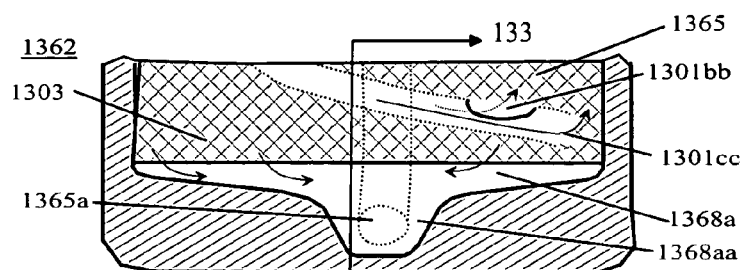
FIG. 13d is line drawing of a front view of a SSR shown in FIG. 13a having an outlet section with the outlet tube centered at the bottom and connected to the side wall of the bag.
Figure 13D:
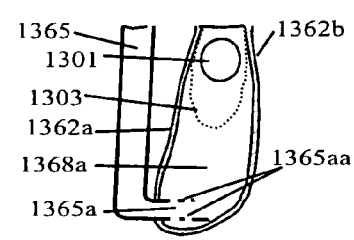

It should be obvious that other designs of SSR 772 shown in FIG. 13*a* can be made without compromising the spirit of the present invention. For example, FIG. 13*d* is a line drawing of the bottom part of another preferred embodiment of a SSR, SSR 1362. FIG. 13*dd* is a line drawing of a cross section taken of FIG. 13*d* along line 133–133'. SSR 1362 is identical to SSR 1366 shown in FIGS. 13*a* and 13*b* except its outlet section 1368*a* is shaped as a funnel and its outlet tube 1365 enters said outlet section through back wall 1362*a* via an angled connection. Here, as for outlet 138*a* of bag 1366, outlet tube 1365 exits outlet section 1368*a* at lowest point, pocket 1368*aa*. The angled connection can be made utilizing, for example, a Halkey-Roberts semi rigid connector # 727AC (St. Petersburg, Fla.) RF welded to wall 1362*a* and then connecting outlet tube 1365 to said connector. This design with an angle connector eliminates the need for outlet tube 1365 to be bent, as is the case for the design of outlet tube 1305 shown in FIG. 13a. Though not illustrated, it is also possible to have outlet tube 1305 contained within blood chamber 138 and exiting at the top of bag 1366.

Figure 13E:
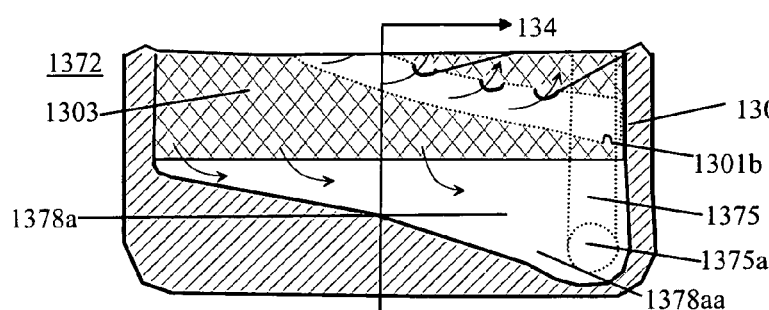
FIG. 13e is line drawing of a front view of a SSR shown in FIG. 13a having a different outlet section with the outlet tube on the side and connected to the side wall of the bag.
Figure 13E:
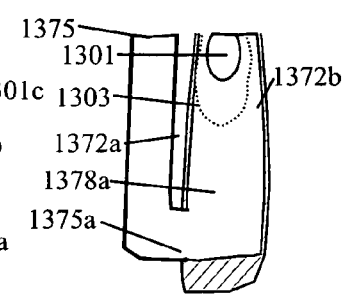

FIG. 13e is a line drawing of the bottom part of another preferred embodiment of a SSR, SSR 1372. FIG. 13ee is a line drawing of a cross section taken of FIG. 13e along line 134–134'. SSR 1372 is identical to SSR 1366 shown in FIGS. 13a and 13b except its outlet tube 1375 enters its outlet section 1378a through back wall 1372a via an angled connection. Here, as for outlet 138a of bag 1366, outlet tube 1375 exits outlet section 1378a at lowest point, pocket 1378aa. The angled connection can be made utilizing, for example, a Halkey-Roberts semi rigid connector # 727AC (St. Petersburg, Fla.) RF welded to wall 1372a and then connecting outlet tube 1375 to said connector. This design with a semi rigid angle connector eliminates the need for outlet tube 1375 to be bent, as is the case for the design of outlet tube 1305 shown in FIG. 13a.

FIGS. 13a and 13b also illustrate a line drawing of one preferred embodiment of a SSR holder that in combination with supporting plate 1389 of venous bag 1366 can form a closed housing that can be used for VAVD. Container 1388 can, in one embodiment, consist of continuous vertical walls (e.g. an extruded ellipsoid tube), a bottom and open top 1388f forming an internal chamber having an effective internal diameter (e.g. for an ellipsoid the effective diameter being a function of the major and minor diameters.) Open top 1388f preferably has a smaller opening than that of container 1388, said opening sized to at least allow venous reservoir 1366 with its blood chamber 138 empty, to be dropped into container 1388. The internal diameter of container 1388 is sized to prevent blood chamber 138 from over extending beyond aforementioned desirable limits. The perimeter of cover 1389 preferably is larger than opening 1388f so as to close said opening 1388f of container 1388 and form sealed chamber 1309.

When positioned properly, supporting plate, or cover, 1389 closes said opening 1388f forming housing 1309. In one embodiment, cover 1389 preferably has two protrusions along its perimeter, 1389e and 1389f, said protrusions forming a channel between accepting open perimeter 1388a of container 1388. This combination lines up cover 1389 and container 1388, provides a better seal, and hinders cover 1389 from sliding off container 1388.

Rim 1388a along the open perimeter of housing 1388 may incorporate sealing gasket 1382 against which cover 1389 can seal when vacuum is applied to chamber 1309. When regulated vacuum is applied, via port 1308 shown in FIG. 13b, SSR 1366 can be used to enhance venous drainage, as described in aforementioned VAVD. For VAVD, the cross section of container 1388 is preferably ellipsoid, a shape that accommodates the general shape of SSR 1366 and provides mechanical strength. It also serves to line up top of bag 1366 with its supported bottom, as well as preventing cover 1389 from rotating and thereby preventing the bag from twisting. Twisting along the vertical axis is also minimized by guides 1388c and 1388b extending from the bottom of container 1388, accepting bag 1366. Preferably, guides 1388b and 1388c support bag 1366 via outlet tube 1305, which is stiffer than pliable wall 1319 and 1318. Container 1388 preferably should be made from crystal clear, rigid, scratch resistance, tough material such as polycarbonate that can withstand an internal pressure of at least −250 mmHg. Since cover 1389 is disposable, it can be made from less expensive material, such as polyvinyl chloride, and need not be clear or scratch resistance. Cover 1389 required the physical strength to withstand the expected pressure differences across its wall when used for VAVD, preferably supporting a minimum internal pressure of −200 mmHg. Structures such as ribs 1389f, shown in FIG. 13a, can be used to reinforce cover 1389. Reducing opening 1388f by extending 1388g shown in FIG. 13b, to "just" allow loading of venous reservoir, reduces the area of cover 1389 that is exposed to vacuum and therefore reduces its required strength.

The top loaded SSR 1366, compared to the bottom loaded design shown in FIG. 8b, has significant advantages. SSR 1366 can be easily placed in the housing with one hand. Once placed, it stays in the holder/housing without clamps (e.g. 88g and 88h in FIG. 8a). With top loading/support, the weight (gravity) of the blood in bag 1366 pulls down cover 1389 against seal 1382 rather than pulling away, thereby using gravity, at least partially, to initiate a seal between cover 1389 and container 1388. Also, the support on top and the weight (blood volume) on the bottom tend to "straightens out" bag 1366. Top loading also provides a single flat plane to seal the bag and its associated tubing within housing 1388. This feature is extremely important to assuring simplicity, reliability, and cost effectiveness. Making one of the walls of the housing a disposable rather than the entire housing as shown in FIG. 9 of PCT '16893, reduces costs significantly. Further reduction in costs is achieved by making the disposable wall, a wall with a small area (e.g. top or bottom wall). A smaller area requires lower force to support the same pressure difference and therefore allows use of thinner cover.

Top loaded SSR has two additional advantages. First, when placing venous reservoir 1366 into its holder by hanging it by it supporting plate 1389, blood in blood chamber 138 tends to settle at the bottom of blood chamber 138 lowering the center of gravity towards the bottom of the venous reservoir and far below, supporting plate 1389. Thus, supported at its top and pulled down by weight of the blood, gravity is used to assist in maintaining the venous reservoir in a vertical position. Second, cover 1389 responds to pressure differences across its wall in a useful manner. Thus, when suction is applied to chamber 1309, cover 1389 pulls tighter against seal 1382; the additional sealing force approximating the product of the area of 1389 exposed to the vacuum applied and the level of vacuum. For example, for a cover 2" wide and 7.5" long, when a suction of −50 mmHg (−1 psi) the sealing force would be 15 lbs. Similarly, should the vacuum fail, and cover 1389 was not secured to ridged housing 1388, a build up of pressure within chamber 1309 would provide a force to open cover 1389 to relief pressure should it rise above atmospheric. Accidental pressure build up due to failed vacuum supply can also be achieved by introducing a small "leak" that prevents total sealing yet is small enough to allow suction in the operating room to overcome that leak and provide the desired regulated vacuum. Such a leak could for example be between 100 and 500 cc/min.

It is obvious that the safety features described with respect to FIG. 8b apply to bag 1366 and housing 1388 shown FIG. 13a. For example, housing 1388 is sized to assure that venous reservoir 1366 cannot over-expand beyond defined limits, said limits defined as a volume in blood chamber 138 that would result in a pressure measured at the top of blood chamber 138 of +10 mmHg. Should blood chamber 138 of venous reservoir 1366 expand, walls 1318 and 1319 would move outward until they make contact with the vertical walls of housing 1388, as shown for walls 18a and 19a in FIG. 8*b*. Once contact is made, further expansion of walls 1318 and 1319 is limited by the vertical walls of rigid housing 1388.

For non-VAVD applications container 1388 need not be sealed. For example, front wall 1388*e* of housing 1388 shown in FIG. 13*b*, can be minimized or eliminated to allow the user to reach bag 1366 without removing the bag from the holder. This still provides a venous reservoir featuring easy top loading and connections of the inlet tube, outlet tube, and purge port to the extracorporeal circuit made by an end user from the top of the venous reservoir. Top connections are easier to make in the operating room than the side or bottom connections required with prior art soft shell venous reservoirs. It should also be obvious that bag 1366 can incorporate additional tubing (e.g. for cardiotomy return) in a manner similar to that shown for inlet tube 1301 and/or outlet tube 1305. The advantage of top loading being maintained as long as said additions allow top cover 1389 to be used as shown. To simplify changing from a closed housing and open front wall housing, front wall 1388*e* of housing 1388, can be designed as a removable wall as described in detail in reference to door 1288 of housing 88 in FIGS. 12*a* and 12*b*.

The aforementioned design of SSR incorporating a disposable supporting plate adds little cost compared to the added convenience and shorter set up time making it economical to use the bag for standard or VAVD procedures. This reduces cost of inventory and simplifies the user's set up and learning curve.

It should be emphasized that all the designs for sealing a venous reservoir having at least one flexible wall within a rigid housing for example, as described in reference to FIGS. 8*b*, 9*b*, 10*b*, 12*b*, or 13*b*, allow the introduction of a venous reservoir into a rigid container without compromising the sterility of the blood contacting surfaces of the venous reservoir. As well known in the art, the blood contacting surfaces of a venous reservoir consist of at least the inside walls of the blood chamber as well as that of the inlet, the outlet, and the air removal tubes. Thus, the present invention overcomes one of the major obstacles, though not mentioned as such in the description of the prior art, inherent in prior art SSR intended to be sealed within a housing, see aforementioned US Pat. '045 and PCT '08734.

Figure 13F:
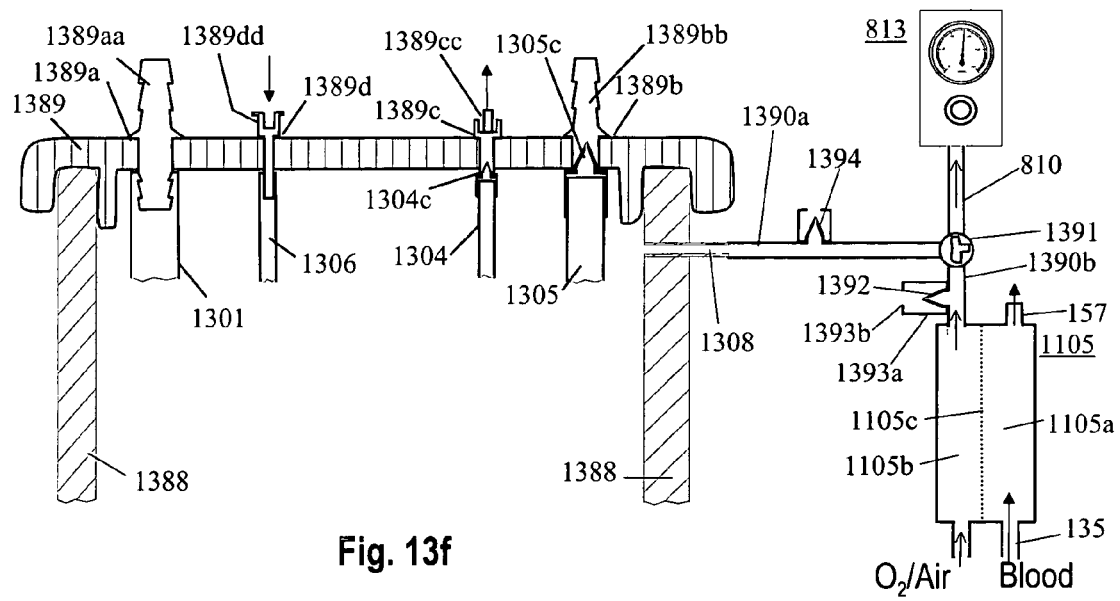
FIG. 13f is line drawing of a preferred embodiment of top cover 1389 shown in FIG. 13a and a combination of components designed to reduce the chance of air crossing the into the arterial line by applying controlled suction to the gas side of the oxygenator.

Cover 1389 may also incorporate tubing connectors 1389*aa*, 1389*bb*, 1389*cc*, and 1389*dd*, shown in FIG. 13*f*, that facilitate assembly of bag tubing and eliminate the need for separate tubing connectors. Thus, inlet tube 1301 is sealed (e.g. solvent bonded) to the bottom of inlet connector 1389*aa*, said inlet connector providing fluid communication between itself and said inlet tubing. Similarly, outlet tube 1305 is sealed to the bottom of outlet connector 1389*bb*, said outlet connector forming fluid communication between itself and said outlet tubing. To further enhance the functionality of outlet connector 1389*bb*, unidirectional valve 1305*c* may be placed within outlet connector 1389*bb*. One-way valve 1305 is a safety feature that prevents back flow from the arterial line, 157 shown in FIG. 1, should arterial pump 1104 stop. Air removal tube 1304 is sealed to the bottom of air removal connector 1389*cc*, said connector forming fluid communication between itself and said air removal tubing. Like connector 1389*bb*, air removal connector 1389*cc* may incorporate unidirectional valve 1304*c*. This valve assures that air cannot enter the bag via connector 1389*cc*. Lastly, infusion tube 1306 is sealed (e.g. solvent bonded) to the bottom of infusion connector 1389*dd*, said infusion connector forming fluid communication between itself and said infusion tubing. An additional advantage of incorporating rigid connectors into cover 1389: they provide physical strength to the cover further preventing buckling under high vacuum.

FIG. 13*f* also illustrates means that assure the pressure on the gas side 1105*c* of microporous oxygenator 1105, not fall below that of chamber 1309. This is achieved by applying the same suction to the outlet of gas port of oxygenator 1105 as is applied to chamber 1309 of FIG. 13*a*. Thus, vacuum is provided by vacuum regulator 813 via tube 818 to three-way valve 1391. Three-way valve 1391 channels the regulated vacuum to tube 1390*a*, said tube in fluid communication with chamber 1309, seen in FIGS. 13*a* and 13*b*, via connector 1308 placed in housing wall 1388, see FIG. 13*f*. Valve 1391 also channels the regulated vacuum to tube 1390*b*, said tube in fluid communication with gas side chamber 1105*b* of oxygenator 1105. Tube 1390*b* is also in fluid communication with one-way valve 1392, caged in structure 1393*a* having opening 1393*b* to atmosphere, said one-way valve opening when pressure in tube 1390*b* exceeds atmospheric pressure. A similar one-way valve 1394, is in fluid communication with tube 1390*a* connecting suction port 1308 of housing 1388 to said three-way valve 1391. Valve 1394 opens when the pressure in tube 1390*a* exceeds atmospheric pressure. Both valves 1392 and 1394 provide safety and assure that in the event vacuum, applied to either tube 1390*a* or 1390*b*, fail, the pressure in said tubes not be built but rather exhaust to atmosphere. It is important the valves 1392 and 1394 have very low cracking pressure, preferably below 10 mmHg. It is also important that these valves present a low resistance to gas flow, preferably requiring no more than 10 mmHg pressure drop at an air flow of 10 L/min. Similarly, vacuum regulator 813, when used to apply suction to oxygenator 1105, should accommodate gas flows exceeding that expected for oxygenator 1105, or 12L/min for adults. Three-way valve 1391 preferably allows the user to apply suction to chamber 1309 via tube 1309*a* but not to oxygenator 1105, apply suction to both chamber 1309 and oxygenator 1105, or not to apply suction to either chamber 1309 or oxygenator 1105.

Applying suction to the gas side of the oxygenator can reduce $O_2$ transfer rate because the partial pressure of $O_2$, $pO_2$, on the gas side is lowered by the percentage decrease in total pressure on the gas side. Thus, when suction of −50 mmHg is applied to the gas side, the total pressure is lowered by 50/760 or 7% thereby nominally reducing the $O_2$ exchange by 7%. Considering that the percent $O_2$ used in the sweep gas is less than 100%, it is possible to compensate for decreased total pressure by increasing the % of $O_2$ in the sweep gas. To avoid reduction in $O_2$ exchange, it is desirable to apply suction to the gas side only when there is none or very low blood flow. Low blood flow can be indicated by low pressure on the blood side. To achieve this desirable result, suction applied to the gas side of the oxygenator is throttled with valve 1391, said valve responding to pressure readings taken of arterial line 157 shown in FIG. 1. For example, when the pressure in line 157 falls below 100 mmHg (a pressure indicating low blood flow), a signal is sent to direct valve 1391 to apply suction to gas exhaust line 1390*b* of oxygenator 1105 shown in FIG. 13*f*. It should be pointed out that the decrease in $O_2$ exchange due to suction application on the gas side (i.e. reduction in $pO_2$) is compensated by longer residence time of the blood (lower blood flow). Applying vacuum to the gas side has no adverse affect on $CO_2$ exchange.

Figure 10A:
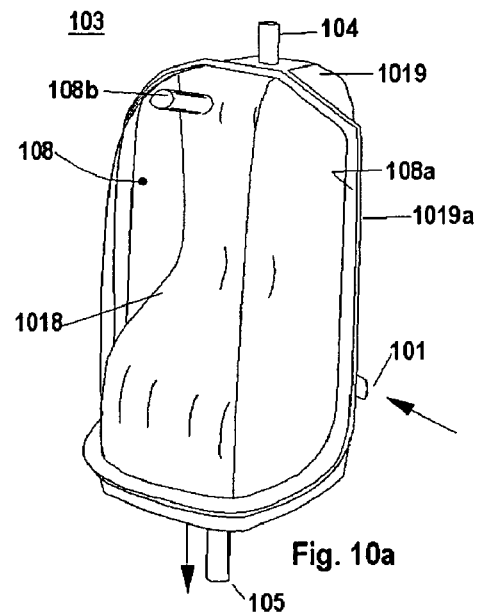
FIG. 10a is a three dimensional rendering of another preferred embodiment illustrating an adaptation of the present invention to other venous reservoir having at least one flexible wall by sealing said flexible wall within a rigid housing such that suction can be applied externally to said flexible wall, thereby providing venous augmentation.
Figure 10C:
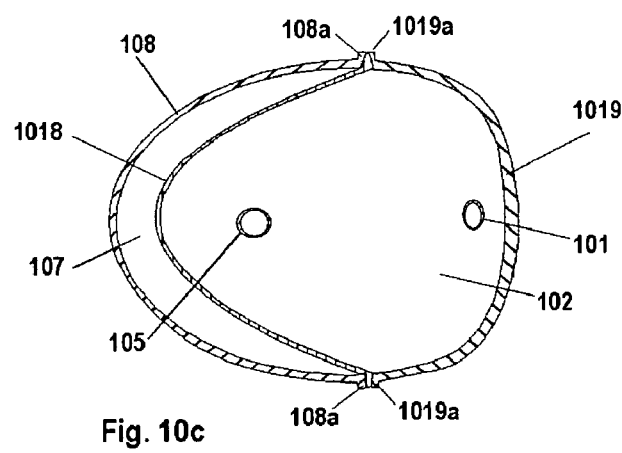

The scope of the invention should not be limited to the aforementioned embodiments. The invention can be extended to other embodiments as illustrated with the venous reservoir having a single flexible wall assigned to Cordis Dow Corp and made by C.R. Bard (U.S. Pat. No. 4,424,190). Currently, there are no means to apply suction to the venous blood utilizing this Bard venous reservoir. With the present invention, applying suction to this design of a venous reservoir is simple. FIGS. 10a, a three dimensional view, 10b, a cross sectional view of 103, and 10c, a cross sectional view along lines 10c and 10c' shown in FIG. 10b, all illustrate a modification of the venous reservoir component shown in FIG. 1 of Pat. '190. Blood enters venous reservoir 103 at inlet 101 into chamber 102, said chamber formed by rigid wall 1019 and flexible wall 1018, shown in a semi-full position. Wall 1018 is also shown in an almost empty position as indicated by dashed line 1018'. Flexible wall is sealed to rigid wall 1019 along periphery 1019a, said seal made by solvent bonding, RF welding, ultrasonic welding or other appropriate method. Air entering expandable blood chamber 102 is extracted via gas exhaust port 104. Gas exhaust port 104 may incorporate an automated gas removal means, as shown for example, utilizing a hydrophobic membrane as described in reference to FIG. 5a. Blood exits via outlet tube 105. For augmented venous return, the present invention adds face plate 108 that seals the external surface of flexible wall 1018 along periphery 108a of face plate 108, forming sealed pressure chamber 107. The seal 108a and seal 1019a therefore can sandwich the free ends of flexible wall 1018 and can be made simultaneously. Gas port 108b is in fluid communication with sealed pressure chamber 107, and is preferably connected to vacuum regulator 813 shown and previously described in reference to FIGS. 8a and 12a. Faceplate 108, is preferably clear and rigid such as clear PVC, polycarbonate, polyethylene terephtalate (PET), polyethylene terephtalate glycol (PETG), polyester, or alike. Faceplate 108 does not have to be biocompatible because it does not contact blood. It should be clear that by incorporating sealing means between faceplate 108 and flexible wall 1018, similar to those described in reference to FIG. 8a, faceplate 108 could be made nondisposable. Whether disposable or not, faceplate 108 forming pressure chamber 107 allows the user to apply suction to chamber 107 via port 108b, said suction transmitted to the blood via flexible wall 1018 thereby providing augmented venous return.

Figure 10B:
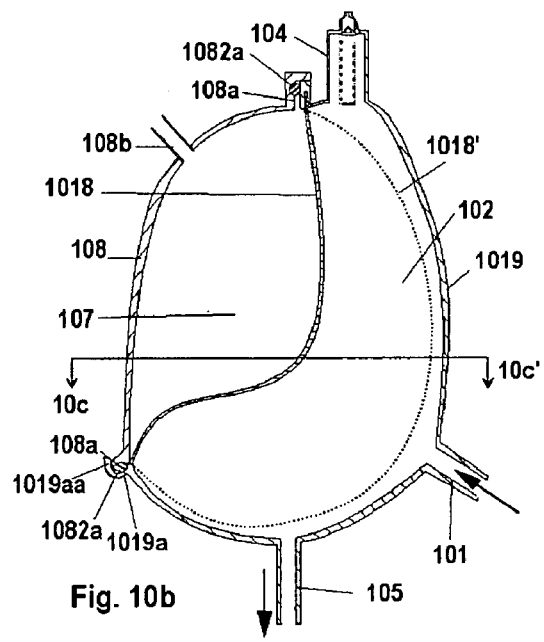

FIG. 10b shows nondisposable cover 108 rests within lip 1019aa of disposable rigid structure 1019 where it is held lightly. When vacuum is applied to suction port 108b of nondisposable cover 108, the user would hold cover 108 against periphery 1019a of structure 1019. Seal material 1082a, located along the periphery of cover 108, is then compressed therebetween forming sealed chamber 107. The suction within chamber 107 pulls disposable structure 1019 and nondisposable cover 108 together. Thus, the pressure difference across faceplate 108 is used for forming a tighter seal and holding cover 108. As described in reference to cover 1389 shown in FIG. 13a, should vacuum fail, any pressure buildup in chamber 107 would push faceplate 108 open to relieve said pressure.

It should be understood that a comprehensive description of each of the applications of the invention is beyond the scope of a patent application and therefore the aforementioned descriptions are given as illustrations and should not be used to limit the intent, spirit, or scope of the invention. With that in mind,

I claim:

1. An apparatus to trap and remove air bubbles in a venous side of a cardiopulmonary bypass circuit, said apparatus comprising;
   a) a blood chamber having an inlet, an outlet and an air venting port to remove air entering the blood chamber;
   b) automated means to detect air in venous blood and provide a signal to alarm the user of the presence of air;
   c) a suction means to remove air from the blood chamber; wherein the alarm signal is used to automatically control the suction means to remove air from the venous blood in the blood chamber.

2. The apparatus of claim 1, wherein the suction means removes air but not blood from the blood chamber.

3. The apparatus of claim 1, wherein the suction means is provided by a roller pump.

4. The apparatus of claim 1, wherein the suction means is provided by wall suction in the operating room.

5. A method to trap and remove air bubbles in the venous side of a cardiopulmonary bypass circuit, said method comprising;
   a) detecting air in the venous side and providing a signal to alarm the user of the presence of air;
   b) removing air from a blood chamber in the venous side; and automatically controlling a suction means to remove air from the venous side of the blood chamber.

6. The method of claim 5, wherein the removing step removes air but not blood from the blood chamber.

7. The method of claim 5, wherein the suction means is provided by a roller pump.

8. The method of claim 5, wherein the suction means is provided by wall suction in the operating room.

9. An apparatus to trap and remove air in the blood on the venous side of a cardiopulmonary bypass circuit, said apparatus comprising:
   a) a blood chamber having an inlet and an outlet;
   b) an air purging port located for removing air entering the blood chamber; and
   c) suction means for automatically removing the air from the blood chamber;
wherein a fluid path between the blood chamber and the suction means is unhindered by the blood.

10. The apparatus of claim 9, wherein the suction means is configured to remove air but little or no blood from the blood chamber.

11. The apparatus of claim 10, wherein the suction means comprises a roller pump.

12. The apparatus of claim 10, wherein the suction means comprises wall suction in the operating room.

13. The apparatus of claim 9, further comprises a vacuum regulator interposed between the blood chamber and the suction means.

14. The apparatus of claim 13, wherein further the blood chamber has a minimum acceptable blood level having a first height above a bottom of the blood chamber, and further having a chimney that extends above a top of the blood chamber by a height equal to at least the first height, and wherein suction applied to the chimney is controlled to pull the blood up into the chimney and maintain the blood in the chimney, thereby removing air that enters the chimney.

15. The apparatus of claim 9, wherein the suction means is configured to maintain air-to-blood interface between the suction means and the blood chamber.

16. The apparatus of claim 9, wherein the controlled suction means comprises a valve that opens to apply suction to a top of the blood chamber to remove air from the top of the blood chamber and closing once at least some of the air has been removed.

17. The apparatus of claim 9, further comprising a one way valve placed between a top of the blood chamber and the suction means.

18. A method to trap and remove air bubbles from the venous side of a cardiopulmonary bypass circuit, said method comprising:
 a) introducing venous blood into a closed blood chamber through an inlet;
 b) allowing the air from the venous blood to rise to the top of the blood chamber;
 c) providing a blood-to-air-interface in the blood chamber;
 d) automatically suctioning the air from the air side of the blood-to-air-interface.

19. The method of claim 18, wherein the blood-to-air-interface minimizes blood loss from the blood chamber when the air is removed from the chamber.

20. The method of claim 18, further comprising means that reduce blood loss from the blood chamber when the air is removed from the blood chamber.

21. The method of claim 18, further comprising means to break up blood foam into blood liquid and thereby reduce blood loss from the blood chamber.

22. A method of claim 21 wherein the means to break up blood foam is a defoamer that provides a defoaming action above the blood-to-air-interface while limiting contact between the defoamer and the blood in the blood chamber.

23. An apparatus to trap and remove air bubbles in the venous side of a cardiopulmonary bypass circuit, said apparatus comprising:
 a) a blood chamber in the venous side having an inlet, an outlet, and an air purging port located at a top of the blood chamber and used to remove air entering the blood chamber;
 b) a suction source for removing the air at the top of the blood chamber; and
 c) a valve, placed between the top of the chamber and the suction source, said valve opening to remove air from the blood chamber and closing once air has been removed.

24. The apparatus of claim 23, wherein the suction source comprises a suction regulator.

25. A method for automatically removing air from venous blood during cardiopulmonary bypass comprising:
 a) having venous blood flow into a closed blood chamber through an inlet port, and out through an outlet port;
 b) maintaining a first blood level in the blood chamber;
 c) letting air in the venous blood rise to a portion of the blood chamber to displace the blood and lower the level of the blood from the first blood level; and
 d) applying controlled suction to automatically remove air from the portion of the blood chamber.

26. An apparatus to trap and remove air in the venous side of a cardiopulmonary bypass circuit, said apparatus comprising;
 a) a blood chamber in the venous side having an inlet, an outlet and an air purging port located at a top of the blood chamber;
 b) a suction means to remove the air from the top of the blood chamber; and
 c) a valve placed between the top of the blood chamber and the suction means;
wherein when air enters the top of the blood chamber, the valve automatically opens, applying suction to the top of the blood chamber and removing the air from the blood chamber.

27. An apparatus to trap and remove air in the venous side of a cardiopulmonary bypass circuit, said apparatus comprising:
 a) a blood chamber in the venous side having a an inlet and an outlet;
 b) an air purging port located for removing air entering the blood chamber;
 c) suction means for automatically removing the air from the blood chamber; and
 d) a fluid path between blood in the blood chamber and the suction means having an inside diameter between 1/32" and 1",
wherein when air enters the top of the blood chamber, the suction means automatically apply suction to the top of the blood chamber and remove at least some of the air from the blood chamber.

28. The apparatus of claim 26, wherein the valve prevents blood from exiting the top of the blood chamber.

29. The apparatus of claim 16, wherein the valve prevents the blood from exiting the top of the blood chamber.

30. The method of claim 18, wherein the blood-to-air-interface assures that blood from the blood chamber does not exit the blood chamber.

31. The combination of an apparatus to trap and remove air in the venous side of a cardiopulmonary bypass circuit and a blood trap, said combination comprising:
 a) a blood chamber in the venous side having a an inlet and an outlet;
 b) an air purging port located for removing air entering the blood chamber;
 c) suction means for automatically removing the air from the blood chamber; and
 d) a blood trap interposed between the suction means and the air purging port;
wherein blood that exits the air purging port is trapped by the blood trap and may be returned to the patient thereby reducing blood loss.

32. The combination of claim 31, wherein the blood trap is a cardiotomy reservoir.

33. The apparatus of claim 1, wherein the suction means removes all the air while limiting blood loss from the blood chamber.

34. The apparatus of claim 1, further comprising means that limit blood loss from the blood chamber via the purge port.

35. The apparatus of claim 34, wherein means that limit blood loss is includes achieved by maintaining air at the top of the blood chamber.

36. The apparatus of claim 34, wherein means that limit blood loss is include a blood-to-air-interface at the top of the blood chamber.

37. The apparatus of claim 34, wherein means that limit blood loss consists of breaking up blood foam into blood liquid.

38. The apparatus of claim 36 wherein the means to limit blood loss is a defoamer that provides a defoaming action above the blood-to-air-interface.

39. The method of claim 5, further comprising means that limit blood loss from the blood chamber via the purge port.

40. The method of claim 39, wherein blood loss is limited by maintaining a blood-to-air-interface at the top of the blood chamber.

41. The method of claim 39, wherein blood loss is limited by breaking up of blood foam, that forms by the venous air bubbling through blood, into blood liquid.

42. A method of claim 41 wherein the blood foam breaking up into blood liquid occurs between the suction means and the blood-to-air-interface.

43. The combination of claim 32, wherein suction applied to the blood chamber is also applied to the cardiotomy reservoir.

44. A method to continuously trap and automatically remove air in the venous side of a cardiopulmonary bypass circuit, the method comprising:
   a. placing a blood chamber having a top, an inlet, an outlet and an air purging port in the venous side of the cardiopulmonary bypass circuit;
   b. trapping venous air in the blood chamber;
   c. providing a suction means; and
   d. providing a mean that respond to air in the blood chamber said response resulting in the application of suction to the top of the blood chamber when air is present and stopping the suction when at least some air has been removed from the blood chamber;
wherein the application and stopping of suction in response to air in the chamber automatically remove air in the venous side of the cardiopulmonary bypass circuit.

45. The method of claim 44, wherein the suction removes all the air while limiting blood loss from the blood chamber.

46. The of claim 44, further comprising means that limit blood loss from the blood chamber via the purge port.

47. The method of claim 46, wherein means that limit blood loss include maintaining air at the top of the blood chamber.

48. The method of claim 46, wherein the means that limit blood loss include maintaining a blood-to-air-interface at the top of the blood chamber.

49. The method of claim 46, wherein the means that limit blood loss include breaking up blood foam into blood liquid, said blood liquid remaining in the blood chamber.

50. The method of claim 49 wherein the means to limit blood loss is a defoamer that provides a defoaming action.

51. A method of claim 49 wherein the blood foam breaking up into blood liquid occurs between the suction means and the blood-to-air-interface.

52. The method of claim 50 wherein the defoamer is located between the blood-to-air-interface and the suction means.

53. The method of claim 44 that further includes a cardiotomy reservoir wherein the suction applied to the blood chamber is also applied to the cardiotomy reservoir.

54. The method of claim 44, that further includes means that inhibit air entering the inlet of the chamber from exiting the chamber.

55. The method of claim 54, wherein the means that inhibit air entering the inlet of the chamber from exiting the chamber is a screen placed between the inlet and outlet of the blood chamber.

56. The method of claim 44, wherein that further includes that maintain blood-to-air interface at the top of the blood chamber.

57. A method to trap and automatically remove air in the venous side of a cardiopulmonary bypass circuit, the method comprising:
   a. having venous blood flow through a blood chamber having a top, an inlet, an outlet and an air purging port;
   b. providing a suction means; and
   c. applying suction to the top of the blood chamber when air is present in the blood chamber to remove air from the top of the chamber and stopping the suction when at least some of that air has been removed;
wherein the application and removal of the suction in response to the air in the chamber automatically removes air in the venous side of the cardiopulmonary bypass circuit.

58. The method of claim 57, that further includes a screen placed between the inlet and outlet of the blood chamber, wherein the screen inhibits air entering the inlet of the chamber from exiting the outlet of the blood chamber.

59. The method of claim 58, that wherein the screen facilitates the upward motion of air entering the blood chamber upward towards air purging port.

60. An apparatus to trap and automatically remove air in the venous side of a cardiopulmonary bypass circuit, the apparatus comprising:
   a. a blood chamber that traps the air in the venous blood, said chamber having a top, an inlet, an outlet, an air purging port;
   b. a suction means connected to the air purging port;
   c. a mean that responds to the air in the blood chamber said response resulting in suction applied to the top of the blood chamber when air is present and stopping the suction when at least some of the air has been removed from the blood chamber;
wherein the application and removal of the suction in response to the air in the chamber automatically remove air in the venous side of the cardiopulmonary bypass circuit.

61. The apparatus of claim 60, that further includes a screen placed between the inlet and outlet of the blood chamber, wherein the screen inhibits air entering the inlet of the blood chamber from exiting the outlet of the blood chamber.

62. The apparatus of claim 61, that wherein further the screen diverts air entering the blood chamber upward towards air purging port.

63. The apparatus of claim 60, further comprising means to break up blood foam into blood liquid and thereby reduce blood loss from the blood chamber.

64. The apparatus of claim 63 wherein the means to break up blood foam is a defoamer.

65. A method to trap and remove air in the venous side of a cardiopulmonary bypass circuit, said method comprising:
   a) providing a blood chamber having an inlet, an outlet, a top, and an air venting port to remove air entering the blood chamber and means that inhibit air entering the inlet of the chamber from reaching the outlet of the chamber;
   b) directing venous blood flow into the inlet of and out of the outlet of the blood chamber;
   c) providing a suction means to remove air from the blood chamber via the air venting port of the blood chamber;
wherein the application and removal of the suction in response to the air in the chamber automatically remove air in the venous side of the cardiopulmonary bypass circuit.

66. The method of claim 18 that further includes placing a screen between the inlet and outlet of the blood chamber, wherein the screen inhibits air entering the inlet of the blood chamber from reaching the outlet of the blood chamber.

* * * * *